(12) United States Patent
Gmeiner et al.

(10) Patent No.: US 9,012,422 B2
(45) Date of Patent: Apr. 21, 2015

(54) METHOD OF TREATING ACUTE MYELOGENOUS LEUKEMIA

(75) Inventors: William H. Gmeiner, Yadkinville, NC (US); Timothy S. Pardee, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 315 days.

(21) Appl. No.: 13/565,108

(22) Filed: Aug. 2, 2012

(65) Prior Publication Data

US 2013/0041018 A1     Feb. 14, 2013

Related U.S. Application Data

(60) Provisional application No. 61/601,218, filed on Feb. 21, 2012, provisional application No. 61/521,940, filed on Aug. 10, 2011.

(51) Int. Cl.
*A61K 48/00*     (2006.01)
*C07H 21/00*     (2006.01)
*A61K 31/7115*     (2006.01)

(52) U.S. Cl.
CPC .................. *A61K 31/7115* (2013.01)

(58) Field of Classification Search
CPC .................................. A61K 31/7115
See application file for complete search history.

(56) References Cited

U.S. PATENT DOCUMENTS

| | | | | |
|---|---|---|---|---|
| 2,885,396 A * | 5/1959 | Heidelberger et al. | .... | 536/28.55 |
| 2,949,451 A * | 8/1960 | Hoffer | ........ | 536/28.54 |
| 2,970,139 A * | 1/1961 | Duschinsky et al. | ........ | 536/26.2 |
| 3,041,335 A * | 6/1962 | Hoffer | .......... | 544/227 |
| 5,614,505 A * | 3/1997 | Gmeiner et al. | ........ | 514/50 |
| 5,663,321 A * | 9/1997 | Gmeiner et al. | ........ | 536/25.5 |
| 5,741,900 A * | 4/1998 | Gmeiner et al. | ........ | 536/25.31 |
| 6,342,485 B1 * | 1/2002 | Gmeiner | ........ | 514/44 R |
| 2007/0072178 A1 | 3/2007 | Haferlach et al. | | |
| 2008/0280774 A1 | 11/2008 | Burczynski et al. | | |
| 2010/0261781 A1 | 10/2010 | Gmeiner | | |
| 2014/0088300 A1 * | 3/2014 | Schmitz et al. | ........ | 536/24.5 |

OTHER PUBLICATIONS (R) M. J. O'Neil et al. (eds.), "The Merck Index, 14th Edition," Merck & Co., Whitehouse Station, NJ, 2006, only pp. 702 supplied (see entry 4112 for "Floxuridine").*
Liao et al. A novel polypyrimidine antitumor agent FdUMP[10] induces thymineless death with topoisomerase I-DNA complexes. Cancer Research. Jun. 1, 2005; 65(11): 4844-4851.
International Search Report and Written Opinion, PCT/US2012/049728, mailed Nov. 2, 2012.

* cited by examiner

*Primary Examiner* — Lawrence E Crane
(74) *Attorney, Agent, or Firm* — Myers Bigel Sibley & Sajovec, P.A.

(57) ABSTRACT

The present invention relates to active compounds for treating acute myelogenous leukemia (AML) in a subject in need thereof and methods of treating AML carried out by administering the subject an active compound in an amount effective to treat the leukemia. The active compound comprises a 10-mer oligonucleotide covalently linked via 3' to 5' phosphodiester linkages of 5-fluorodeoxyuridine, FdUMP[10], or a pharmaceutically acceptable salt thereof.

20 Claims, 12 Drawing Sheets

A

- Control
- p53 shRNA

B

C

- Control
- p210
- MN1

A

B

C

A

B

A

B

C

A

B

METHOD OF TREATING ACUTE MYELOGENOUS LEUKEMIA

RELATED APPLICATIONS

This application claims the benefit of U.S. Provisional Patent Application Ser. No. 61/601,218, filed Feb. 21, 2012, and of U.S. Provisional Patent Application Ser. No. 61/521,940, filed Aug. 10, 2011, the disclosures of which are incorporated by reference herein in their entirety.

STATEMENT REGARDING GOVERNMENT SUPPORT

The present invention was made with government support under Grant Number P30CA012197 from the National Cancer Institute and CA102532 from the NIH. The US Government has certain rights to this invention.

STATEMENT REGARDING ELECTRONIC FILING OF A SEQUENCE LISTING

A Sequence Listing in ASCII text format, submitted under 37 C.F.R. §1.821, entitled 9151-172_ST25.txt, 699 bytes in size, generated on Nov. 25, 2014 and filed via EFS-Web, is provided in lieu of a paper copy. This Sequence Listing is hereby incorporated by reference into the specification for its disclosures.

FIELD OF THE INVENTION

The present invention concerns methods of treating acute myelogenous leukemia in a subject in need thereof.

BACKGROUND OF THE INVENTION

Acute myelogenous leukemia (AML; also known as "acute myeloid leukemia") is an aggressive malignancy that leads to marrow failure, and death. AML affects approximately 12,000 people per year in the United States, causing 9,000 deaths[1]. Despite decades of research, standard therapy has not changed and the overall 5-year survival rate is 30-40%[2]. The current standard of care for patients with AML is induction chemotherapy with cytarabine (Ara-C) and an anthracycline[2]. Most patients treated this way will achieve a complete, but transient, remission. Once relapsed, the disease is increasingly resistant to further therapy. Age is an important prognostic factor in AML[3]. For patients 60 years of age or older the prognosis is grave. There are biological and clinical differences in older patients, resulting in a five-year survival rate of less than 10%[4]. These differences include increased co-morbidities resulting in higher early death rates, more patients with high-risk cytogenetic profiles and multidrug resistance phenotypes[2]. This is compounded by the fact that AML is a disease of the elderly with the median age-of-onset of 72 years old[5]. The high rate of early mortality and resistance has led some to question whether elderly patients with AML benefit from therapy at all[6]. There is a clear need for additional therapies with acceptable toxicity profiles.

SUMMARY OF THE INVENTION

A first aspect of the invention is a method of treating acute myelogenous leukemia in a subject in need thereof, comprising administering said subject an active compound as described herein in an amount effective to treat said leukemia. In some embodiments, the active compound comprises a 10-mer oligonucleotide of 5-fluorodeoxyuridine (SEQ ID NO:1), hereinafter FdUMP[10], or a pharmaceutically acceptable salt thereof.

In some embodiments, the subject is administered a single active compound consisting of said FdUMP[10] or pharmaceutically acceptable salt thereof in an amount effective to treat the leukemia.

A further aspect of the invention is an active agent as described herein for use in carrying out a method of treatment as described herein, and/or for the preparation of a medicament for carrying out a method of treatment as described herein.

U.S. Pat. No. 6,342,485 to Gmeiner describes synergistic combinations of nucleic acid directed chemotherapeutic agents such as 5-fluorouracil (5-FU) in combination with thymidylate synthase (TS) inhibitors such as FdUMP[10]. The treatment of leukemia is suggested at column 9 line 16. However, it is not suggested that FdUMP[10] would be useful in the absence of an additional chemotherapeutic agent.

DETAILED DESCRIPTION OF PREFERRED EMBODIMENTS

Figure 1:
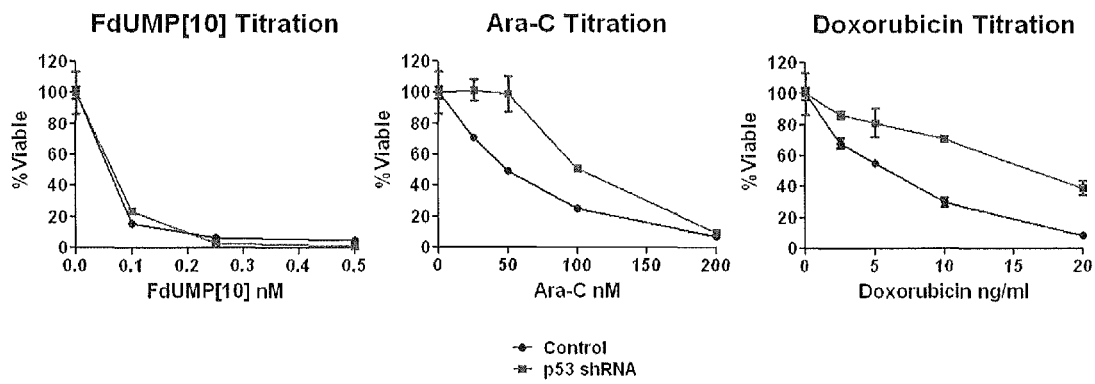
FIG. 1. FdUMP[10] is active against cells expressing adverse prognostic factors. (A) Cytotoxicity assays of murine AML cells that knockdown p53. Cells were exposed to the indicated drugs for 72 hours and then assessed for viability. Viability is shown as percentage of control; error bars represent the standard error. (B) Flow cytometry of Annexin V assay. Cells expressing the p53 short hairpin RNA (shRNA) were exposed to the indicated drug for 48 hours and then labeled with Annexin V and propidium iodide (PI). (C) Cytotoxicity assays of murine AML cells expressing either the meningioma (disrupted in balanced translocation) 1 gene (MN1) or the breakpoint cluster region-Abelson murine leukemia viral oncogene homolog 1 fusion gene (BCR-ABL, p210). Cells were exposed to the indicated drugs for 72 hours and then assessed for viability. Viability is shown as percentage of control; error bars represent the standard error.
Figure 1:
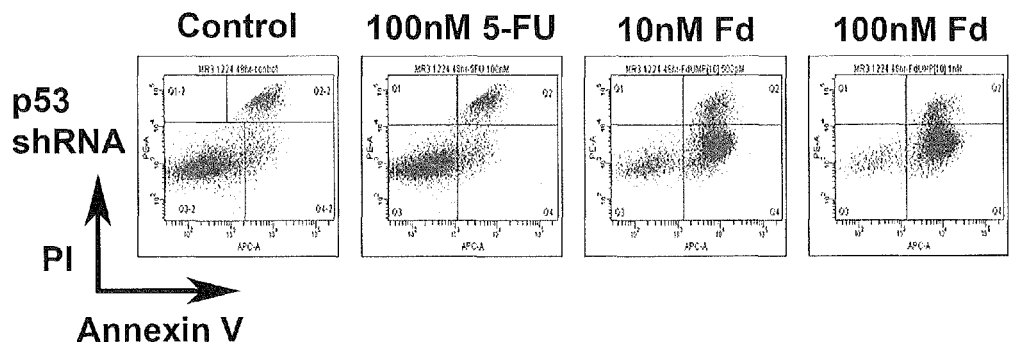
Figure 1:
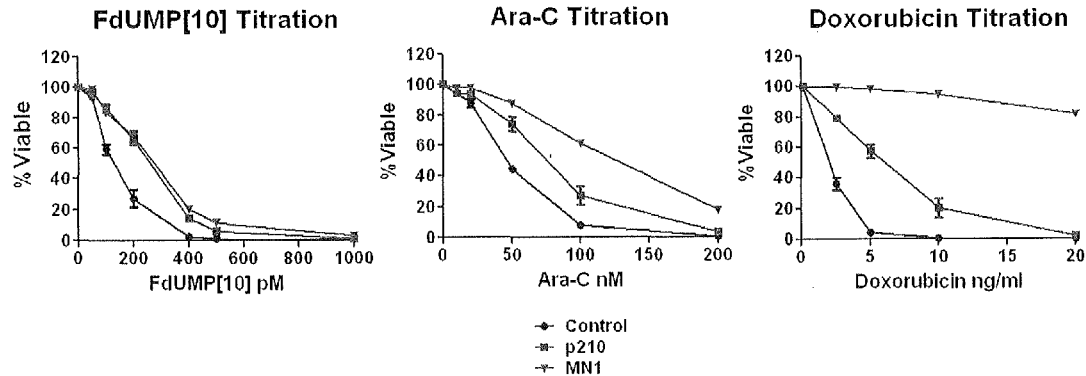

The present invention is primarily concerned with the treatment of human subjects, but the invention may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects. In some embodiments, the subjects are human subjects at least 60, 65, or 70 years old.

"Acute myelogenous leukemia" as used herein may be any type of AML, including but not limited to (by the WHO classification) therapy related AML, AML with multilineage dysplasia, and AML with characteristic genetic abnormalities; and/or (by the French-American British (FAB) classification) minimally differentiated acute myeloblastic leukemia, aute meyloblastic leukemia without maturation, acute myeloblastic leukemia with granulocytic maturation, acute promyelocytic leukemia, acute myelomonocytic leukemia, myelomonocytic together with bone marrow eosinophilia, acute monoblastic leukemia, acute monocytic leukemia, acute erythroid leukemia, acute megakaryoblastic leukemia, and acute basophilic leukemia.

"Treat" as used herein refers to any type of treatment that imparts a benefit to a subject or patient, including but not limited to reducing symptoms, eliminating symptoms, delaying the onset of symptoms, slowing the rate of progression of symptoms, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active Compounds.

Active compounds used to carry out the present invention are, in general, oligonucleotides of 5-FU, particularly oligonucleotides containing 8, 9, 10, 11, or monomers of 5-fluorodeoxyuridine covalently linked via 3' to 5' phosphodiester linkages. Particularly preferred is the 10-mer oligonucleotide of 5-fluorodeoxyuridine, FdUMP[10], having the structure:

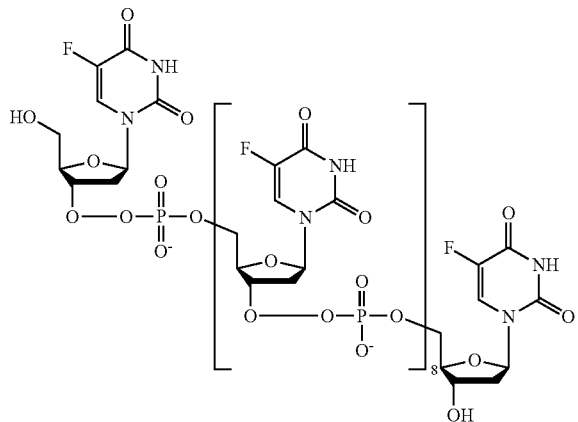

FdUMP[10]

Such compounds are known and described in, for example, U.S. Pat. Nos. 5,457,187 and 6,342,485, the disclosures of which are incorporated by reference herein in their entirety.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Subjects, Dosage and Routes of Administration.

As noted above, any of a variety of different subjects may be treated by the methods of the present invention.

While in some embodiments the subject may be one categorized as in a good prognostic risk category (that is, a subject that has a high probability of cure), in other embodiments the subject may be one who is categorized in an intermediate prognostic risk category, and in still other embodiments the subject may be one who is categorized in a poor (or adverse) prognostic risk category. Numerous prognostic markers or factors for categorizing AML subjects or patients for likely outcome of treatment are known. See, e.g., J. Foran, *New Prognostic Markers in Acute Myeloid Leukemia: Perspective from the Clinic*, Hematology 2010, pages 47-55; D. Grimwade and R. Hills, *Independent prognostic factors for AML Outcome*, Hematology 2009, pages 385-395. Prognostic markers or factors the presence of which indicate a subject is in a good (or better risk) prognostic risk category include, but are not limited to:

cytogenetic markers such as: t(8;21)(q22;q22); inv(16) (p13.q22); t(16;16)(p13.q22); and t(15;17); and/or molecular markers or such as normal cytogenetics with a nucleophosmin gene (NPM1) mutation or a CCAAT/enhancer binding protein-alpha (CEBPA) mutation in the absence of Fms-like tyrosine kinase 3 internal tandem duplications (FLT3-ITD).

Prognostic markers or factors the presence of which indicate a subject is in an intermediate prognostic risk category include, but are not limited to:

cytogenetic markers such as: normal cytogenetics, +8, t(3; 5); t(9;11)(p22q23); and other non-defined, and/or molecular markers or abnormalities such as the protooncogene c-Kit (c-KIT) mutation with t(8;21)(q22;q22), or inv(16)(p13,q22),t(16;16) (p13.q22).

Prognostic markers or factors the presence of which indicate a subject is in a poor (or adverse) prognostic risk category include, but are not limited to:

cytogenetic markers such as a complex karotype (>3 abnormalities); MK+; -5,5q-; -7,7q-; other 11q23 abnormalities [non-t(9;11)]; inv(3)(q21 q26.2), t(3;3)(q21 q26.2); t(6;9), t(9;22); abnormal(17p); and/or molecular abnormalities such as high Ena/VASP-like protein splice variant (EVL1) expression (with or without 3q26 cytogenetic lesion); normal cytogenetics with FLT3-ITD in the absence of NPM1 mutation.

In some embodiments, the subject has or expresses: a mixed lineage leukemia (MLL) fusion protein such as the MLL-eleven nineteen leukemia (MLL-ENL) fusion protein, the BCR-ABL fusion protein, FLT3 internal tandem duplications (FLT3-ITD), a deleted or mutated p53, high or elevated (as compared to normal subjects) levels of meningioma 1 (MN1), and/or high or elevated (as compared to normal subjects) levels of lactate dehydrogenase, all shown or indicated to confer an adverse prognosis for AML.

In some embodiments; the subject is afflicted with relapsed AML (e.g., the subject was previously treated for AML, then in partial or complete remission for AML, and then the AML has returned).

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, intravenous, and/or transdermal administration.

The therapeutically effective dosage of any specific compound, the use of which is in the scope of present invention, will vary somewhat from compound to compound, and patient to patient, and will depend upon the condition of the patient and the route of delivery.

In some embodiments, the active compound is administered to the subject intravenously.

In some embodiments, the active compound is administered to the subject in an amount of from 100, 200 or 400 mg/m$^2$ to 800 or 1000 mg/m$^2$ (e.g., 1 to 5 times weekly, for a period of from 4 to 6 weeks per cycle).

The present invention is explained in greater detail in the following non-limiting Examples.

EXAMPLE 1

The novel fluoropyrimidine FdUMP[10] is a polymer of the TS-inhibitory fluoropyrimidine (FP) metabolite 5-fluoro-2'-deoxyuridine-5'-O-monophosphate (FdUMP). Since its discovery, 5-FU has been widely used to treat multiple solid tumors including breast, colon, and head/neck cancers[7] however, it is seldom used in hematologic malignancies including the acute leukemias. The mechanism of action for 5-FU is thought to involve both the inhibition of TS and disruption of RNA processing. Toxicities associated with 5-FU treatment include myelosuppression, diarrhea, and mucositis. These toxicities overlap with the drugs currently used in AML; thus 5-FU has not been considered an attractive candidate for AML treatment. In contrast, FdUMP[10] was 338-fold more potent in the NCI 60 cell line screen relative to 5-FU[8]. FdUMP[10] uniquely targets both TS and topoisomerase 1 (Top1). FdUMP[10], but not 5-FU, is highly active towards the human leukemia cell lines included in the NCI 60 and has shown enhanced potency and lower toxicity relative to 5-FU in mouse xenograft models[8-9]. The favorable safety profile for FdUMP[10], combined with its enhanced activity led us to investigate whether this compound has activity against AML.

Materials and Methods:

Cell Culture and Viability Assays.

OCI-AML3 cells were a kind gift of Dr Mark Minden at University of Toronto. All human cell lines were maintained in RPMI media (Gibco, Carlsbad, Calif.) supplemented with 10% FBS, penicillin and streptomycin. Cells were grown at 37° C. with 5% CO$_2$. Viability assays were done using the Cell Titer-Glo assay (Promega, Madison, Wis.) according to the manufacturer's protocol. All murine cells were derived from fetal liver cells infected with MLL-ENL alone or with a mutation of glycine at amino acid 12 to aspartate of NRAS (NRAS$^{G12D}$) or FLT3-ITD expressing vectors[10]. Murine cells were maintained in stem cell media (40% DMEM, 40% IMDM, 20% FBS, supplemented with murine SCF to 10 ng/ml, murine IL6 to 2 ng/ml, and murine IL3 to 0.4 ng/ml).

Primary AML Samples and Normal Human HSCs.

All samples were collected under an IRB-approved protocol. Primary AML samples were from 15 patients with confirmed AML (see Table 3). All patients gave written informed consent. All samples were obtained during clinically-indicated procedures. Cells were collected by centrifugation, resuspended in ACK lysis buffer (150 mM NH$_4$Cl, 10 mM KHCO$_3$, 0.1 mM EDTA) at room temperature for 5 minutes, centrifuged again, washed with PBS, and stored at −80° C. until use. Alternatively, cells were isolated by Ficoll-gradient centrifugation and stored as above. Normal hematopoietic stem cells (HSCs) were obtained from healthy allogeneic stem cell transplant donors. Cells were obtained from granulocyte macrophage colony-stimulating factor (GM-CSF)-primed apheresis of peripheral blood, Ficoll separated, and stored as above.

Colony Formation Assays.

Human cell lines, primary patient samples or normal human HSCs, were thawed and incubated in Stem SpanS-FEM media supplemented with Stem Span CC100 cytokine cocktail (StemCell Technologies, Vancouver, BC) for 24 hours with the indicated drug. Cells were then placed in ColonyGEL High Cytokine Formulation media (ReachBio, Seattle, Wash.). Experiments were performed in triplicate. Colonies of eight or more cells were counted on or after day 7.

Western Blots and Immunofluorescence.

Samples were lysed in Laemmli buffer, separated by SDS-PAGE, and transferred to an Immobilon PVDF membrane (Millipore, Billerica, Mass.). Antibodies against p53 (IMX25, 1:1000; Leica Microsystems), TS (#35-5800, 1:1000; Invitrogen), Topoisomerase I (556597, 1:2000; BD Pharmingen) and actin (AC-15, 1:5000; Abcam) were used. For immunofluorescence studies of phosphorylated γH2AX, cells were fixed with 4% NBF, permeabilized with PBS containing 0.2% Triton-X 100, and probed with anti-phosphoH2AX (#2577, 1:100; Cell Signalling Technologies) followed by donkey anti-rabbit Alexa Fluor 594 conjugated antibody (1:500, A-21207; Invitrogen) and visualized via fluorescence microscopy.

In Vivo Treatment Studies.

The Wake Forest University Institutional Animal Care and Use Committee approved all mouse experiments. Luciferase-tagged leukemia cells were transplanted into 6- to 8-wk-old sublethally irradiated recipient mice (4.5 Gy) by tail-vein injection of 1×10$^6$ viable cells. Mice were monitored by bioluminescent imaging on day 7. Imaging was performed using an IVIS100 imaging system (Caliper LifeSciences, Hopkinton, Mass.). Mice were injected with 150 mg/kg D-Luciferin (Gold Biotechnology, St. Louis, Mo.), anesthetized with isoflurane, and imaged for 2 min. Chemotherapy was initiated upon detection of clear signals. Mice were treated with 300 mg/kg FdUMP[10] or 5-FU at 121 mg/kg (APP Pharmaceuticals, Schaumburg, Ill.) or the combination of 125 mg/kg cytarabine and 3.75 mg/kg doxorubicin (both from Bedford Laboratories, Bedford, Ohio) by jugular or tail vein injection. Control animals were injected with PBS. Repeat luciferase imaging was performed on day 6 of treatment.

Toxicology Studies and Murine Bone Marrow Transplantation.

Normal C57/Bl6 mice were treated with identical dose, schedule and route of each drug as in the efficacy studies (i.e. Day 1, 3, 5 and 7). 72 hours after the last dose, animals were sacrificed, bilateral femoral cells harvested and organs fixed in 10% neutral buffered formalin followed by routine tissue processing and sectioning for hematoxylin and eosin staining. Slides were then reviewed by a veterinary pathologist using a Nikon Eclipse 50i light microscope. Photographs of tissues were taken using the NIS Elements D3.10 camera and software system. For transplant studies Ly5.1+C57/Bl6 recipient animals were irradiated to 8 gray and injected with 1×10$^6$ femur cells or, when 1×10$^6$ cells were not isolated, then 90% of all cells isolated by tail vein injection. Three weeks later recipient femoral bone marrow was harvested and stained with APC-conjugated anti-Ly5.2 antibody (BD Pharmingen, San Diego, Calif.) and analyzed by flow cytometry.

Apoptosis Assays.

Cells were seeded in 6-well plates at 25,000 cells/ml in 3 mls, grown for 2 days and treated with the indicated drug for 16, 24, 36, or 48 hours. After centrifugation and washing in cold PBS cells were stained with PI (Sigma Aldrich, St. Louis, Mo.) and APC-conjugated Annexin V in a binding buffer (0.1 M Hepes (pH 7.4), 1.4 M NaCl, and 25 mM $CaCl_2$ solution) (BD Pharmingen, San Jose, Calif.) according to the manufacturer's protocol. Flow cytometric analysis was conducted on a BD FACS Cantoll cytometer with the BD FACSDiva software (BD Biosciences, San Jose, Calif.).

TS Catalytic Activity.

Cells were plated at $1.5 \times 10^6$ cells in 100 $mm^2$ plates and grown overnight in RPMI 1640 medium with 20% FBS. Cells were exposed to the indicated drug for 8, 16, 24, or 48 hours. Cells were then harvested in 25 mM Tris-HCl, pH 7.4 with Complete Protease Inhibitor Cocktail (Roche), put through 2 freeze/thaw cycles, and vortexed. The lysates were centrifuged at 10,000×g for 10 minutes at 4° C. TS assays were performed in a final volume of 200 μl containing 75 μM 5,10 methylene tetrahydrofolate in 0.5 M NaOH (Schircks Laboratories, Switzerland), 10 μM dUMP, 200,000 dpm of $^3$H-dUMP (Moravek Biochemicals), 100 μM 2-mercaptoethanol, and 25 mM $KH_2PO_4$, pH 7.4. Cell lysate (400 μg of protein) was added to the reaction buffer. Reactions were incubated at 37° C. for 30 minutes and stopped by addition of 100 μl of 20% TCA, incubated for 5 minutes on ice. 200 μL of activated charcoal solution (10 g activated charcoal, 0.25 g BSA, 0.25 g dextran sulfate, in 100 ml of water) was added, vortexed and maintained at room temperature for 10 minutes. Reactions were centrifuged at 10,000×g for 30 minutes. 200 μL aliquots of the supernatant were read by scintillation counting. All reactions were repeated a minimum of three times.

ICE Bioassay/Top1 Cleavage Complex Detection.

Cells were plated at $1.5 \times 10^6$ cells in 100 $mm^2$ plates and grown in RPMI 1640 medium with 20% FBS. Either 100 nM 5-FU or 1 nM FdUMP[10] were added and incubated for 24 or 48 hrs. Cells were lysed in 2 ml of 1% sarkosyl in 1×TE pH 7.5 and frozen at −20° C. Samples were homogenized approximately 25 times. Addition of 1 ml of sarkosyl was used to wash the homogenizer. CsCl gradients were made as in[9]. The samples were overlaid and ultracentrifuged in a SW41T rotor. Centrifugation was at 36K for 20-22 hours at 20° C. 500 ml fractions were collected. Fractions 6 through 11 were used for analysis. 200 ul of each fraction and an equal volume of 25 mM $NaPO_4$ buffer (pH 6.5) were loaded onto a nitrocellulose membrane using a Schleicher and Schuell Minifold II slot blotter. The membrane was blocked with 5% milk in TBST. Primary antibody was added at 1:500 dilution, overnight at 4° C. Secondary antibody was used in the same manner. ECL Lightning Plus (Perkin Elmer) was used for detection of the TOP1 cleavage complex.

Statistical Analysis:

All means were compared by two tailed student's T test. Survival curves were estimated by the Kaplan-Meier method and p values were determined by the log rank test. P values below 0.05 were considered significant. Analysis was performed using Graph Pad Prism version 5.02 (Graph Pad Software Inc).

Results

FdUMP[10] is Highly Active In Vitro Against Multiple Human Leukemia Cell Lines.

To assess the activity of FdUMP[10] against human leukemia cell lines, we performed in vitro cytotoxicity assays. We exposed HL60, OCI-AML3, Jurkat, THP-1, K562, and KG1a cells to varying concentrations of FdUMP[10] for 72 hours and then determined viability. All human leukemia lines had $IC_{50}$ values in the low nanomolar range (see Table 1). To compare activity of FdUMP[10] to other standard chemotherapies using this assay, we also treated cells with 5-FU, cytarabine, or doxorubicin. We chose to use doxorubicin as the anthracycline as it is the best tolerated anthracycline in C57/Bl6 mice[11] and would allow for comparisons between in vivo and in vitro studies. The $IC_{50}$ values for 5-FU were all ~1000 times higher than for FdUMP[10] despite the fact that on a molar basis there is only a tenfold increase FP content (Table 1). Although we observed a wide range of sensitivities to cytarabine and doxorubicin, all cell lines had similar responses to FdUMP[10], implying a lack of cross-resistance. These data demonstrate that FdUMP[10] is more active against a variety of human leukemia cell lines than 5-FU, cytarabine, or doxorubicin.

FdUMP[10] is Highly Active Against Murine AML Models Expressing Different Poor Prognostic Markers.

The human cell lines tested have different adverse prognostic factors yet they all had similar $IC_{50}$ values for FdUMP [10] (Table 1) suggesting that these factors may not modulate response to FdUMP[10]. To determine the effects of these markers we utilized a genetically defined mouse model system. This model is based on expression of MLL-ENL and has been shown to alter its chemotherapy sensitivity in response to expression of different prognostic markers[10].

TABLE 1

$IC_{50}$ values for FdUMP[10], 5-FU, Doxorubicin and Cytarabine

| Treatment | HL60 | Jurkat | THP-1 | K562 | KG1a | OCI-AML3 |
|---|---|---|---|---|---|---|
| FdUMP [10] | 3.4 nM (2.984 to 3.825) | 5.4 nM (4.609 to 6.417) | 4.1 nM (3.413 to 4.907) | 21.5 nM (14.85 to 30.99) | 4.9 nM (3.995 to 6.043) | 5.5 nM (5.111 to 6.006) |
| 5-FU | 5.0 μM (3.804 to 6.643) | 7.5 μM (6.169 to 9.100) | 1.2 μM (0.9425 to 1.421) | 7.0 μM (3.270 to 15.03) | 5.3 μM (3.902 to 7.139) | ND |
| Doxorubicin | 21.7 nM (18.90 to 24.97) | 75.2 nM (48.16 to 117.47) | 160.5 nM (75.7 to 340.5) | 252.9 nM (200.69 to 319.14) | 1.3 μM (1.19 to 1.51) | ND |
| Cytarabine | 144.9 nM (85.00 to 247.0) | 15.5 nM (14.44 to 16.67) | 6.7 μM (5.890 to 7.534) | 83.7 nM (72.24 to 96.94) | 195.8 nM (163.5 to 234.4) | 133.6 nM (59.41 to 300.6) |

95% confidence intervals are shown in the parenthesis
ND = Not determined

FdUMP[10] was highly active against multiple MLL-ENL expressing cell lines with $IC_{50}$ vales in the picomolar range (Table 2). This included a cell line expressing the human FLT3 receptor containing an internal tandem mutation (FLT3-ITD) shown to confer a worse prognosis in AML patients[12] and alter chemotherapy response[10].

TABLE 2

IC$_{50}$ values of FdUMP[10], 5-FU, Doxorubicin and Cytarabine

| Chemotherapy | MFL2 | MR2 | M1 |
|---|---|---|---|
| FdUMP[10] | 131.4 pM | 124.2 pM | 123.8 pM |
|  | (108.3 to 159.3) | (97.9 to 157.7) | (111.5 to 137.6) |
| 5-FU | 292.3 nM | 214.0 nM | ND |
|  | (251.8 to 339.4) | (178.9 to 255.9) |  |
| Doxorubicin | 24.6 nM | 11.4 nM | 3.7 nM |
|  | (15.9 to 38.1) | (7.2 to 18.2) | (3.4 to 4.2) |
| Cytarabine | 54.4 nM | 71.8 nM | 46.8 nM |
|  | (58.4 to 182.7) | (75.9 to 166.5) | (43.5 to 50.4) |

MFL2 = MLL-ENL + Flt3 ITD
MR2 = MLL-ENL + NRas$^{G12D}$
M1 = MLL-ENL alone
95% confidence intervals are shown in the parenthesis.

Figure 8:
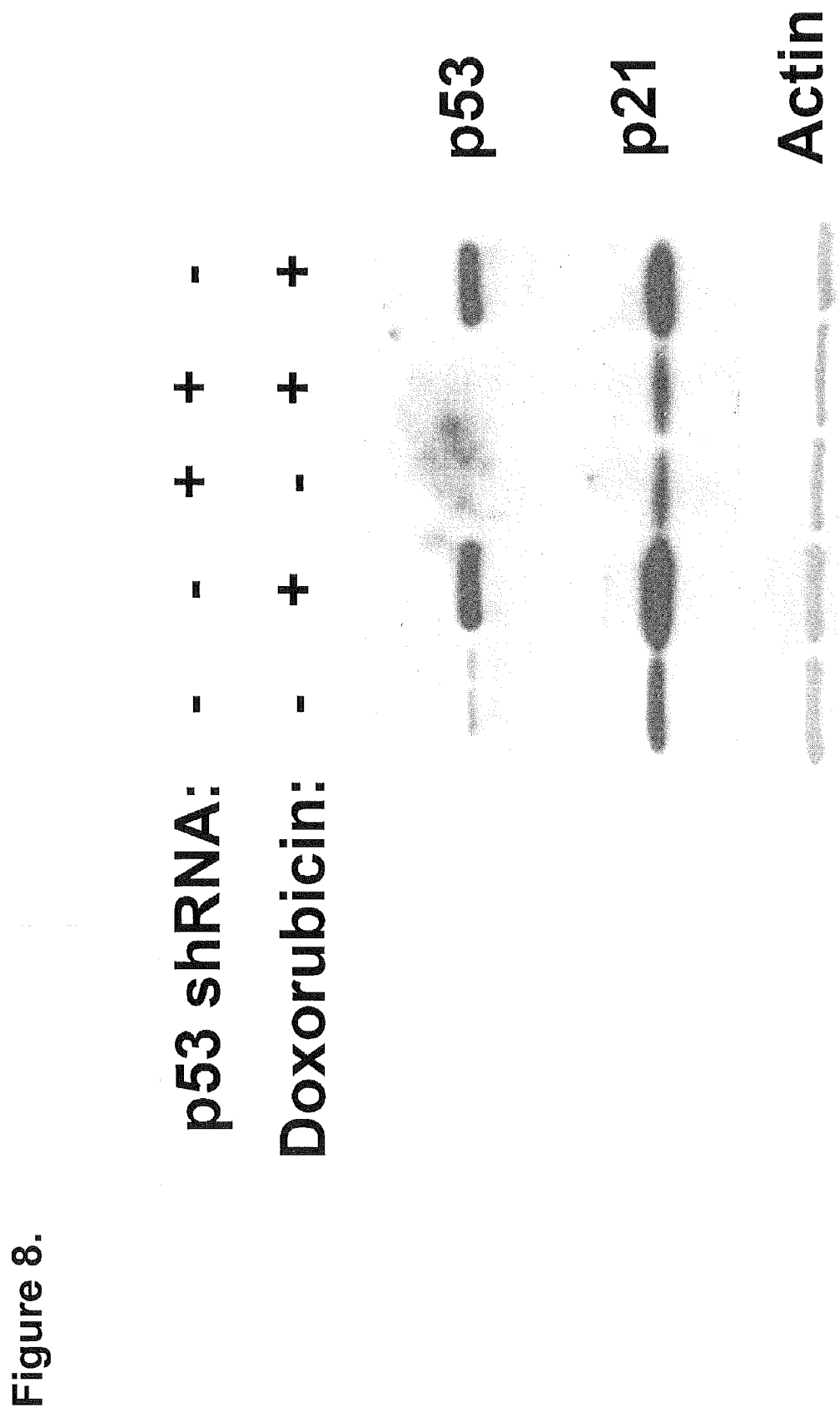
FIG. 8. p53 shRNA efficiently suppresses p53 induction. Murine AML cells expressing either a p53 shRNA or control vector were exposed to 500 ng/ml doxorubicin for 4 hours, then lysed and blotted for p53, p21, and actin as shown. An uninfected control is shown in the far right lane.

Most of the human leukemia lines tested have deleted or mutated p53. p53 activation is important for response to cytarabine[13] and doxorubicin[14] and its loss is associated with a worse prognosis in AML[15-16]. To determine if p53 is important in response to FdUMP[10], we infected an MLL-ENL- and FLT3 ITD-expressing cell line with either a control or p53-targeting shRNA vector. Cells expressing the shRNA showed loss of p53 induction indicating efficient knockdown (FIG. 8). Loss of p53 response led to resistance to both doxorubicin and cytarabine (FIG. 1A). However, there was no change observed for FdUMP[10], suggesting that p53 is not required for response. To determine if p53-suppressing cells are undergoing apoptosis in response to FdUMP[10], we performed an Annexin V assay. Cells treated with FdUMP[10] were positive for Annexin V binding, suggesting a p53-independent apoptotic pathway (FIG. 1B).

In addition to p53 loss, several other adverse prognostic factors are expressed in the cell lines tested. K562 cells express the fusion gene BCR-ABL that has been implicated in chemotherapy resistance[17] and prognosis in AML[18]. THP-1 cells express high levels of MN1[18], shown to confer an adverse prognosis[20-21]. To test the effects of these genes on FdUMP[10] response we infected a murine AML cell line with vectors expressing human MN1 or the p210 BCR-ABL (p210) fusion protein. Cells expressing either p210 or MN1 displayed resistance to doxorubicin with IC$_{50}$ values that were 2.95 and >10 fold higher than the parental leukemia cells and to Ara-C with MN1 expressing cells having a 3.2- fold increase in IC$_{50}$ value (FIG. 1C). In contrast, FdUMP[10] remained highly effective for cells expressing either p210 or MN1 with IC$_{50}$ values that changed by only 1.98 or 2.07 fold respectively (FIG. 1C). These results indicate that factors conferring resistance to Ara-C and doxorubicin minimally affect response to FdUMP[10] and suggest FdUMP[10] is likely to have activity in patients with these poor prognostic markers.

FdUMP[10] is Highly Active Against Human AML Stem Cells while Sparing Normal HSCs.

Figure 2:
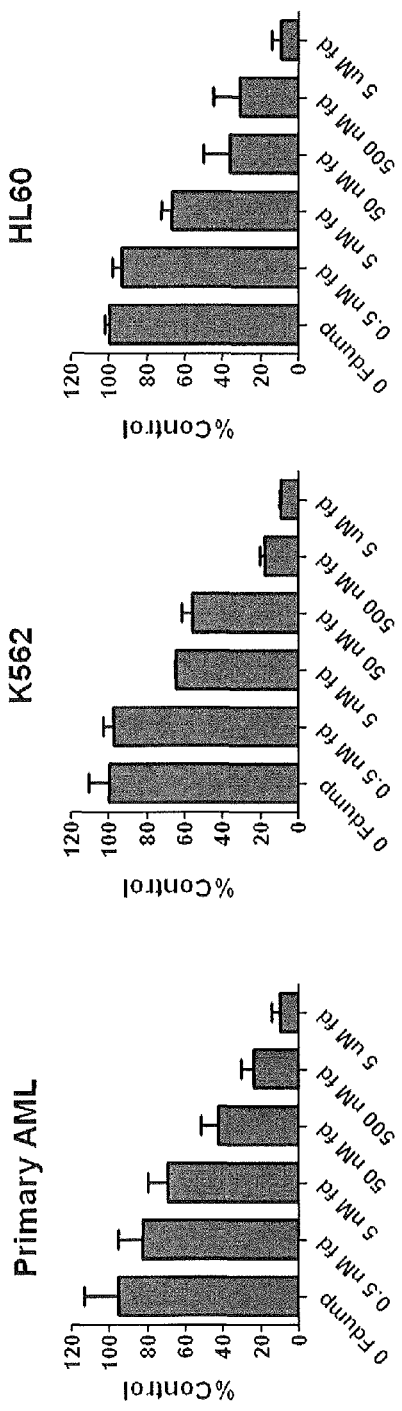
FIG. 2. FdUMP[10] is active against leukemia stem cells from cell lines and primary patient samples. (A) Colony formation assays. Primary patient samples or cell lines were incubated with the indicated drug for 24 hours and placed in methylcellulose media. Plates were read on or after day 7. All concentrations were done in triplicate. Primary AML is the combined results of three independent primary patient samples. Colony numbers are normalized to controls and error bars represent the standard error. (B) Colony formation assays. As in (A), the result shown is the combination of four separate normal HSC donors.
Figure 2:
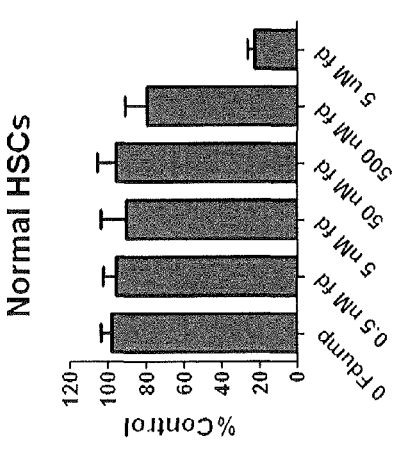

The existence of human leukemia stem cells (LSCs) has been widely established and their persistence in treated patients is thought to be responsible for relapse (reviewed in[22]). To determine if FdUMP[10] had activity against LSCs, we performed colony formation assays using K562 and HL60 cells as well as three primary patient samples (samples A10-A12, Table 3). FdUMP[10] was highly effective in suppressing colony formation from the cell lines as well as from the primary patient samples (FIG. 2A) demonstrating that FdUMP[10] has activity against human LSCs. In order to establish the effect of FdUMP[10] on normal HSCs we performed colony assays on HSCs from four separate healthy allogeneic donors. In contrast to its effect on LSCs, FdUMP[10] only suppressed HSC colony formation at the highest dose tested (FIG. 2B) suggesting a large therapeutic window.

FdUMP[10] Causes Inhibition of Thymidylate Synthase and Trapped Topoisomerase I Cleavage Complexes in Human Leukemia Cells.

Figure 3:
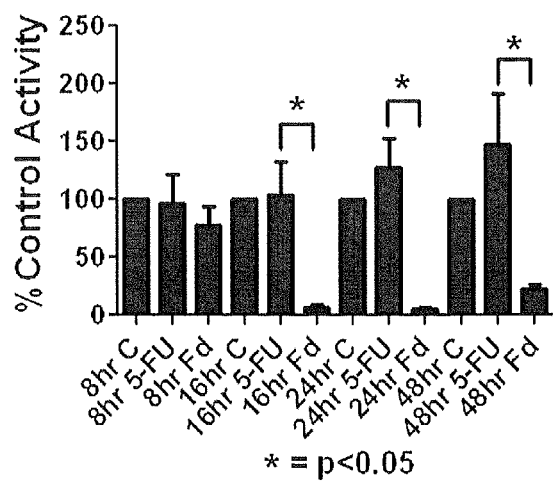
FIG. 3. FdUMP[10] is a potent inhibitor of thymidylate synthase and traps topoisomerase 1 (Top1) cleavage complexes. (A) TS inhibition assay. HL60 cells were exposed to 10 nM FdUMP[10] or 100 nM 5-FU for the indicated time, lysed and assayed for TS activity. Activity is plotted as percentage of control. Error bars represent standard errors of the mean. (B) ICE bioassay for Top1 cleavage complexes. THP-1, Jurkat and HL60 cells were incubated with 100 nM FdUMP[10] for the indicated time. Cells were lysed and subjected to ICE bioassay (see methods), and DNA-containing fractions were blotted for Topo I. (C) Results of TS and Top1 Western blots. K562 (K), HL60 (H), Kg1a (Kg), mixed lineage leukemia-eleven nineteen leukemia (MLL-ENL) murine AML (M3), or 3 primary AML patient samples (B1-3) were blotted with the indicated antibody.
Figure 3:
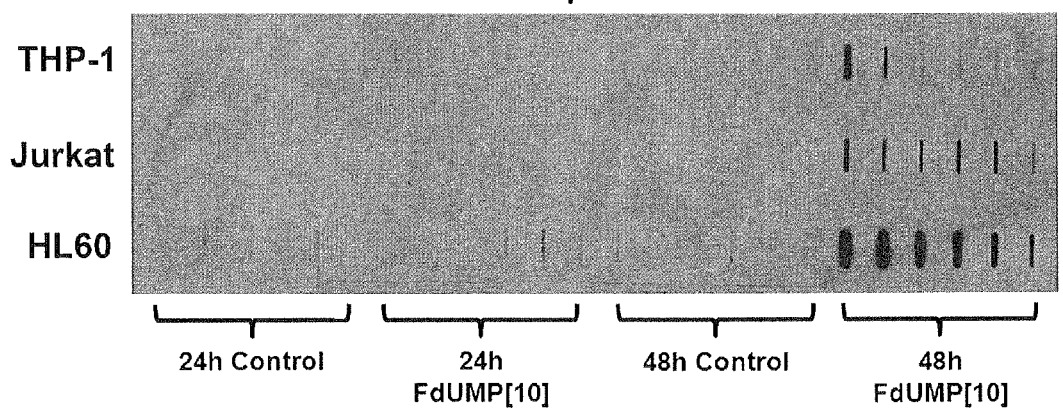
Figure 3:
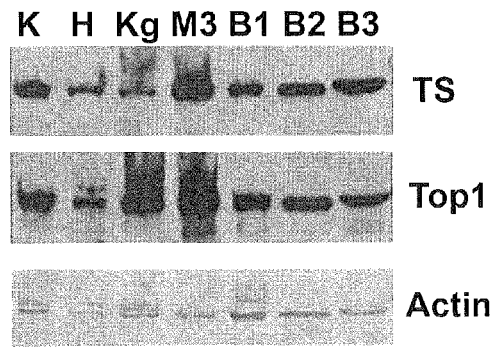

Previous work in human and murine lymphoblastic leukemia cell lines demonstrated that FdUMP[10] induces TS inhibition and trapped topoisomerase I cleavage complexes (Top1CC)[9]. To determine if FdUMP[10] inhibited TS in human AML cell lines, we exposed HL60 cells to 10 nM FdUMP[10] or 100 nM 5-FU and performed assays for activity. FdUMP[10] caused profound and prolonged TS inhibition compared to a 10-fold greater concentration of 5-FU (FIG. 3A). To determine if FdUMP[10] trapped Top1CC, THP-1, Jurkat and HL60 cells were exposed to 100 nM FdUMP[10] for 24 or 48 hours and assessed for the presence of Top1CC. By 48 hours, Top1 was detected co-migrating with genomic DNA, consistent with trapped complexes (FIG. 3B). These data demonstrate that FdUMP[10] causes profound TS inhibition and traps Top1CC. This is in contrast to 5-FU which did not significantly inhibit TS at ten times the concentration of FdUMP[10] despite the fact that the amount of fluoropyrimidine delivered is identical. This would suggest that FdUMP[10] is not simply a more concentrated version of 5-FU but rather has distinct biochemical effects.

Figure 9:
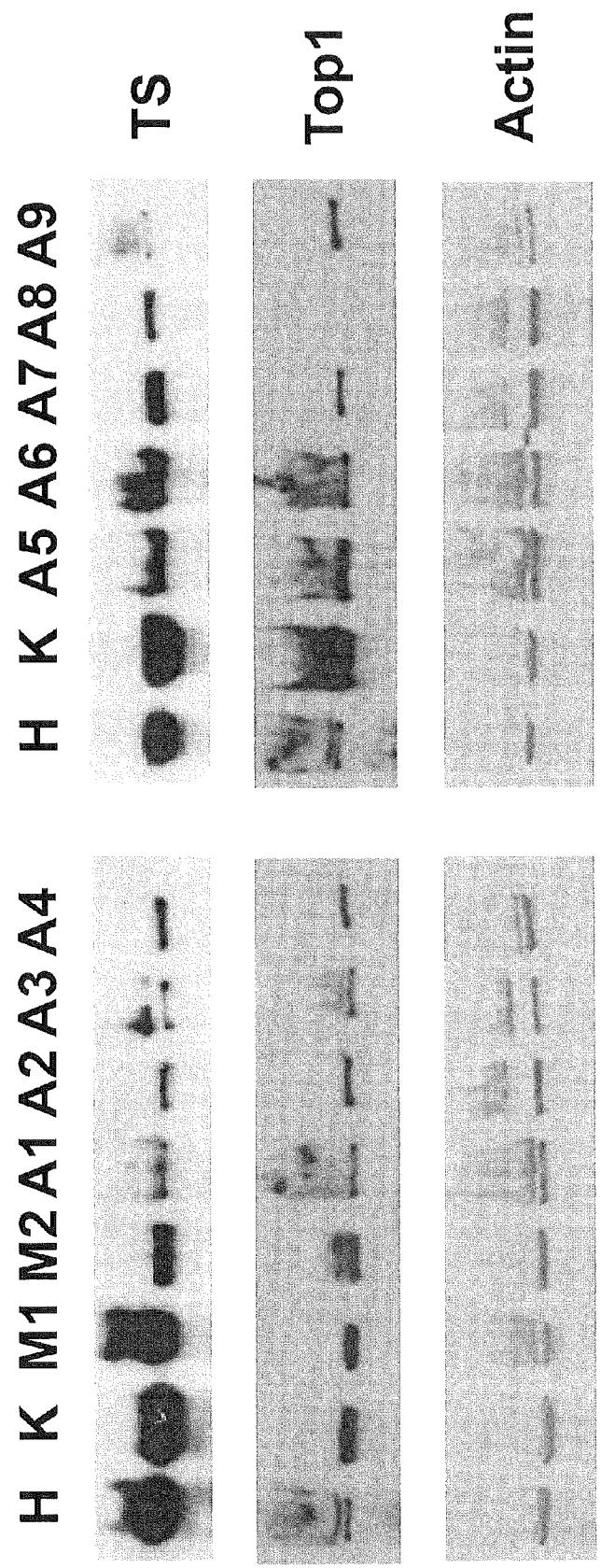
FIG. 9. TS and Top1 are expressed in AML cells. TS and Top1 Western blots. HL60 (H), K562 (K), two MLL-ENL driven murine AML lines (M1 and M2), and nine primary samples from patients with AML samples (A1-A9) were blotted with the indicated antibody.

To determine if TS and Top1 are commonly expressed in AML cells we performed a western blot for TS and Top1 in HL60, K562, KG1a, three murine AML lines and twelve patient samples. Patient characteristics are shown in Table 3. We found wide variability in the expression levels of TS and Top1 (FIGS. 3C and 9). However, there was no clear correlation between TS or Top1 level and FdUMP[10] sensitivity as K562 cells had the highest levels of TS and Top1 expression despite having an IC$_{50}$ approximately seven times higher than HL60 cells (Table 1). Importantly, both proteins were detectable in all but one primary patient sample. These data show that TS and Top1 are commonly expressed in human AML cells and suggest that FdUMP[10] will have broad activity in AML.

TABLE 3

Primary Patient Sample Characteristics

| Sample Name | Sample type | Sex | Age | FAB | Karyotype |
|---|---|---|---|---|---|
| B1 | Bone Marrow | Female | 60 | M5 | Trisomy 8, Trisomy 9 |
| B2 | Bone Marrow | Female | 68 | Non-M3 | 46XX |
| B3 | Bone Marrow | Female | 79 | M1 | 46XX |
| A1 | leukophoresis | Male | 55 | M5 | Trisomy 8 |
| A2 | leukophoresis | Female | 65 | M5 | Trisomy 8, Isochromosome 13 |
| A3 | leukophoresis | Female | 66 | M2 | Deletion 6q, +Flt3 ITD |
| A4 | leukophoresis | Female | 59 | M4Eo | Inversion 16 |
| A5 | leukophoresis | Male | 33 | Non-M3 | Monosomy 7, inversion 3 |
| A6 | leukophoresis | Male | 53 | M5 | 46XY, +Flt3 ITD |
| A7 | leukophoresis | Female | 89 | M4 | Complex |
| A8 | leukophoresis | Female | 59 | Non-M3 | 46XX |
| A9 | leukophoresis | Male | 69 | Non-M3 | 46XY, +Flt3 ITD |
| A10 | Bone Marrow | Female | 39 | Non-M3 | Trisomy 8 |
| A11 | Bone Marrow | Female | 67 | Non-M3 | t(8; 21) |
| A12 | Leukophoresis | Male | 39 | M5b | 46XY, Flt3 ITD+ |

FdUMP[10] Arrests Cells in S-Phase.

Figure 4:
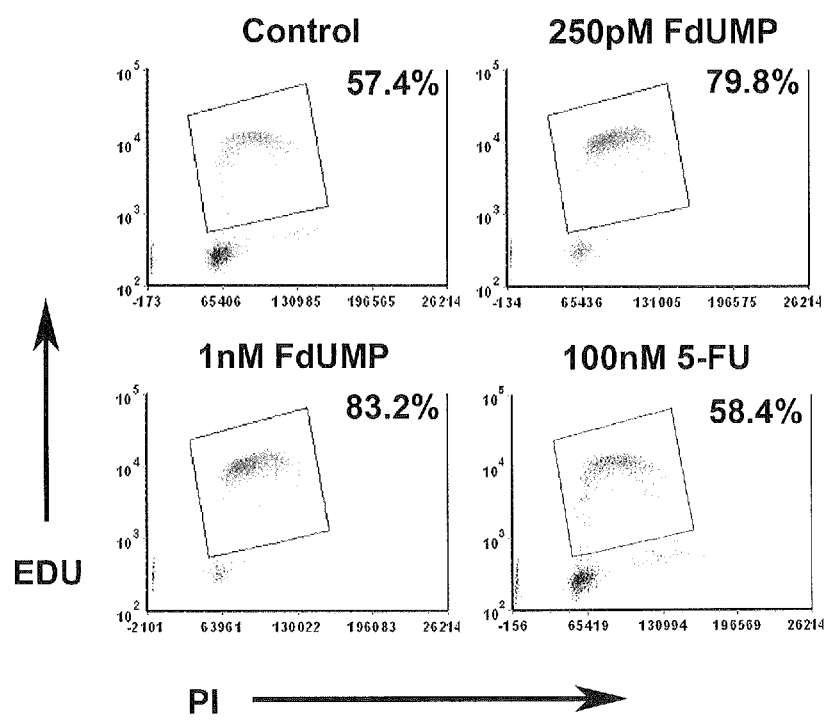
FIG. 4. FdUMP[10] causes S phase arrest regardless of p53 status. (A) EdU incorporation assays. MLL-ENL driven murine AML cells were incubated with the indicated drug for 8 hours and subjected to a 5-ethynl-2' deoxyuridine (EdU) incorporation assay. S phase cells were gated as shown. Percentages shown are for cells in S phase. (B) EdU incorporation assay as in (A). Cells were infected with either a p53 targeting shRNA or a control vector and exposed to the indicated drug for 8 hours.
Figure 4:
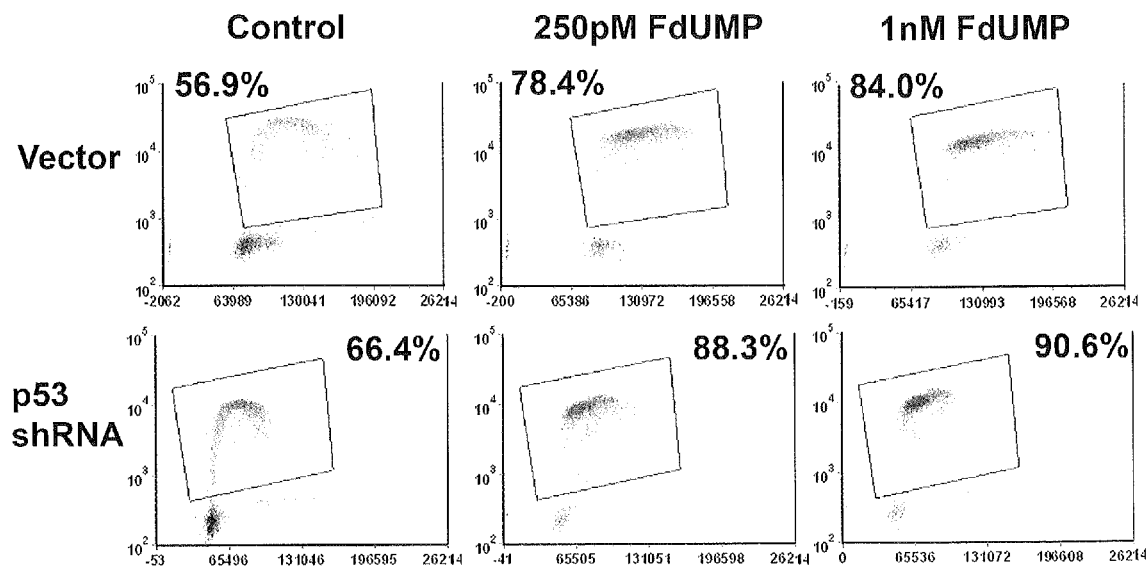

Our results suggest that Top1 complexes at replication forks are trapped by incorporated FdUMP or dUMP, leading to stalled replication forks and ultimately DNA strand breaks. This, coupled to the lack of thymidine would lead to futile cycles of attempted repair and recurrent trapping of Top1[9]. If so, cells exposed to FdUMP[10] should accumulate in S-phase. To assess this possibility, we determined the cell cycle distribution of murine AML cells after exposure to FdUMP[10] for eight hours. As predicted, cells accumulated in S-phase after exposure to FdUMP[10] (FIG. 4A). 5-FU was much less efficient at arresting cells in S-phase, with essentially no difference in the number of cells in S-phase from control even at 100 times the FdUMP[10] concentration (FIG. 4A). An intact p53 response was not necessary for the observed S-phase arrest, as cells expressing a p53 targeting shRNA were also efficiently arrested in S-phase (FIG. 4B). These data confirm that the TS inhibition and trapped Top1CC induced by FdUMP[10] lead to the accumulation of cells in S-phase. The lack of significant accumulation in S-phase of cells exposed to even 100 times higher concentration of 5-FU again demonstrate that FdUMP[10] has distinct biochemical activities and is not simply converted to 5-FU.

FdUMP[10] Induces DNA Damage and Apoptosis in AML Cells.

Figure 10:
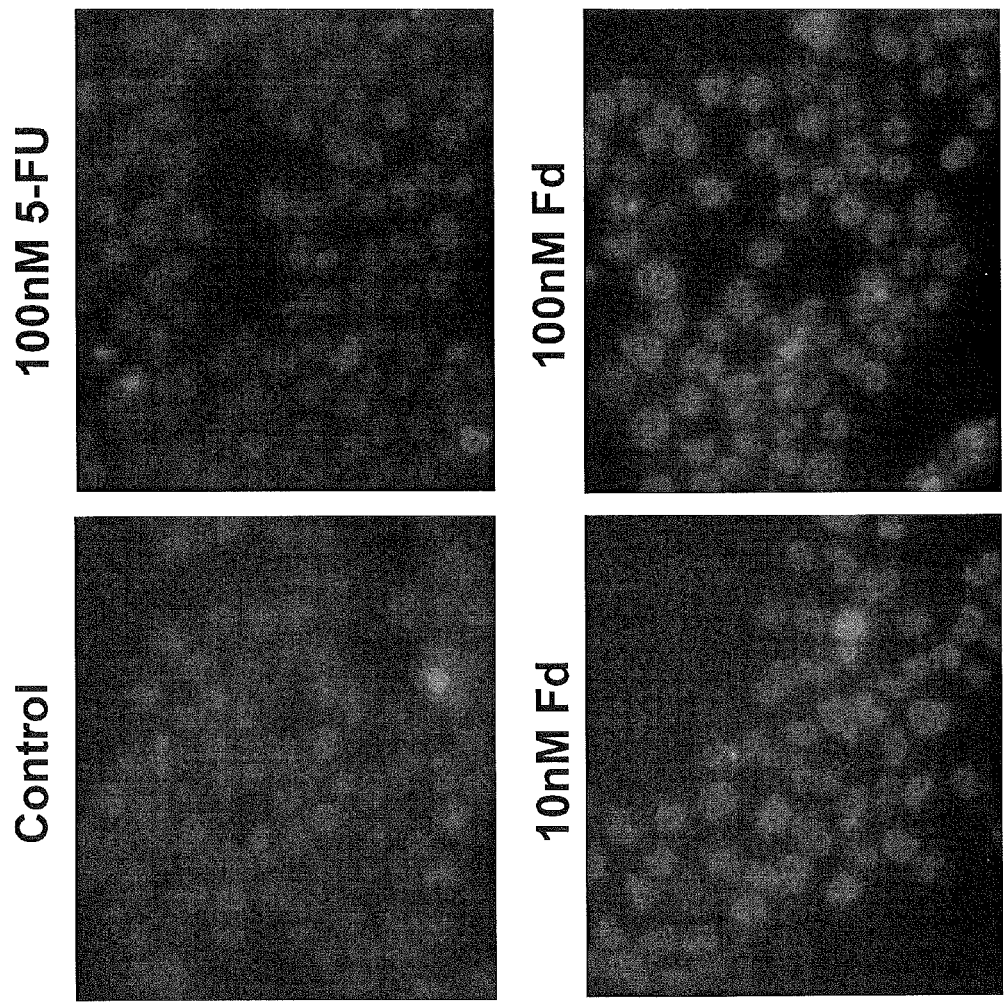
FIG. 10. FdUMP[10] induces DNA damage. Immunofluorescence for γH2AX foci. Jurkat cells were treated with the indicated drug for 24 hours and then assayed for the presence of γH2AX foci. Assay was done and images captured as in FIG. 5.

We have demonstrated that FdUMP[10] induces profound TS inhibition, trapped Top1CC and accumulation of cells in S-phase. This combination of stalled replication, lack of thymidine and trapped Top1CC should lead to the accumulation of DNA double-strand breaks (DSBs). Consistent with this, previous work has shown that FdUMP[10] induces DNA damage[9]. To determine if FdUMP[10] induces DSBs in human AML cells, we performed immunofluorescence assays against γH2AX. K562 cells were exposed to 10 or 100 nM of FdUMP[10] or 1 μM 5-FU for 24 hours and then assessed for γH2AX foci. Exposure to FdUMP[10] at either concentration resulted in the formation of multiple γH2AX foci (FIG. 5A), indicating the induction of DNA DSBs. In contrast, exposure to 1 μM 5-FU under identical conditions did not result in the formation of γH2AX foci, suggesting that FdUMP[10] is much more efficient than 5-FU at inducing DNA damage. A similar result was obtained using Jurkat cells (FIG. 10).

Figure 5:
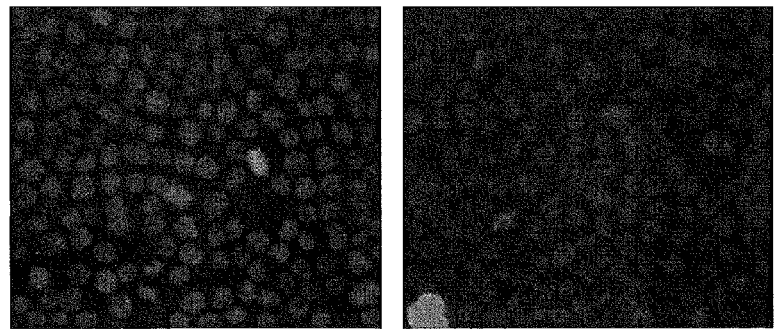
FIG. 5. FdUMP[10] causes DNA damage and induces apoptosis. (A) Immuno-fluorescence for gamma histone H2AX (γH2AX) foci. K562 cells were treated with the indicated drug for 24 hours and then assayed for the presence of γH2AX foci. Secondary antibody was conjugated with Alexa Fluor 594 and Images were captured with an Olympus IX70 inverted fluorescent microscope equipped with a Retiga 2000R digital color camera and using an LPIanFI 20×/0.40 objective. Images were analyzed with Image Pro Plus 5.1 software. (B) Flow cytometry of Annexin V assay. THP-1 or HL60 cells were treated with the indicated drug for 48 hours and then labeled with Annexin V and propidium iodide (PI) and analyzed by flow cytometry.
Figure 5:
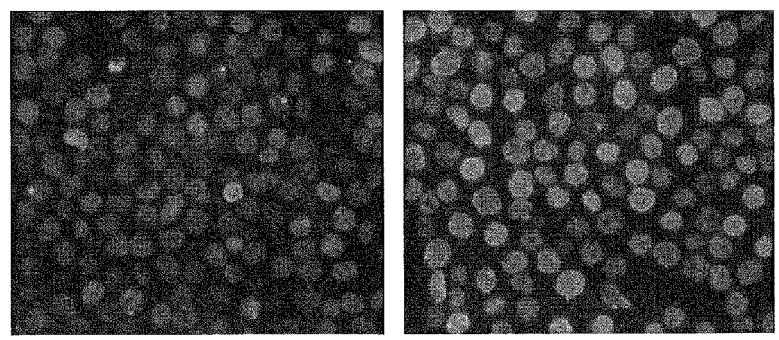
Figure 5:
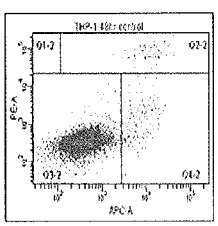
Figure 5:
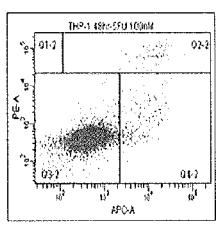
Figure 5:
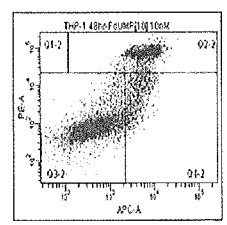
Figure 5:
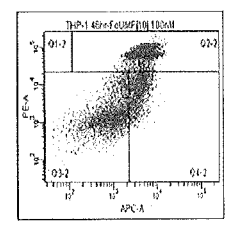
Figure 5:
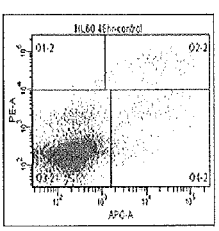
Figure 5:
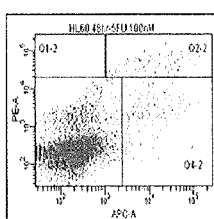
Figure 5:
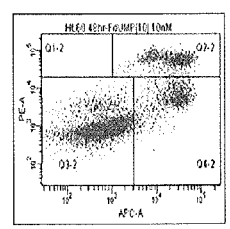
Figure 5:
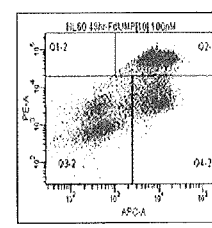
Figure 11:
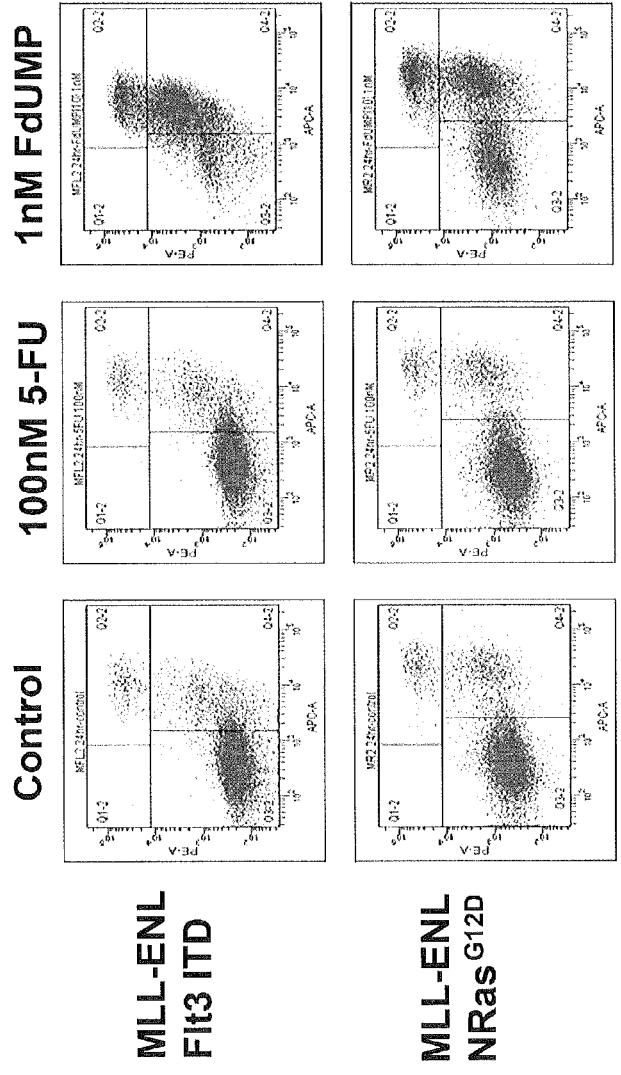
FIG. 11. FdUMP[10] induces apoptosis in murine AML cells. (A) Flow cytometry results of Annexin V assays. The indicated MLL-ENL driven leukemia cells were treated with drug for 24 hours analyzed by flow cytometry, as in FIG. 5. (B) MLL-ENL and neuroblastoma RAS viral oncogene homolog (NRAS) containing AML cells were exposed to the indicated drug for 24 hours and analyzed as in (A).
Figure 11:
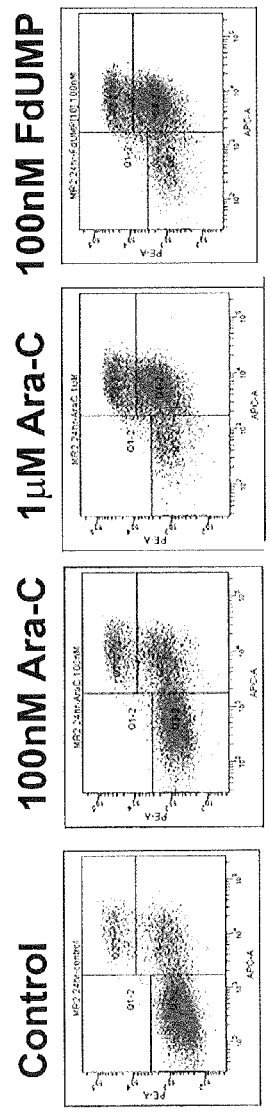

The futile repair cycles and DNA damage induced by FdUMP[10] would be predicted to lead to cell death, possibly by apoptosis. Indeed, previous work has shown that FdUMP[10] induces apoptosis in human colorectal cancer cells[23]. To determine if exposure to FdUMP[10] culminates in apoptosis, we treated THP-1 and HL60 cells with either 10 or 100 nM FdUMP[10] and assessed apoptosis induction by Annexin V and propidium iodide staining. At 48 hours, a majority of cells were stained positive, indicating apoptosis is the predominant cell death mechanism (FIG. 5B). Consistent with the $IC_{50}$ data, 5-FU was far less efficient at inducing apoptosis with only minimal annexin V positive cells, even at 100 nM (FIG. 5B). FdUMP[10] also efficiently induced apoptosis in two separately derived murine AML cell lines (FIG. 11A). As with the human lines, FdUMP[10] was far more efficient at inducing apoptosis than 5-FU or Ara-C (FIG. 11B). Taken together, these data demonstrate that FdUMP[10], but not 5-FU, efficiently induces DNA damage and apoptosis in human and murine leukemia cells indicating a distinct biochemical mechanism for FdUMP[10] relative to 5-FU.

FdUMP[10] is Highly Active Against Murine AML In Vivo.

Figure 12:
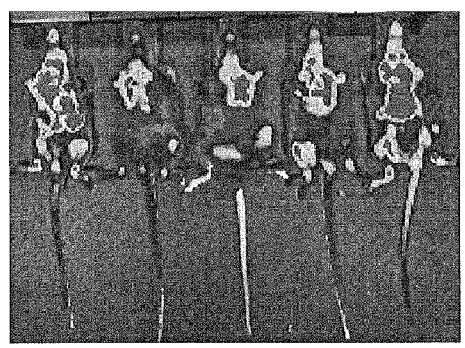
FIG. 12. FdUMP[10] is effective in vivo. (A) Bioluminescence signals of mice on day 6 following treatment. C57/Bl6 mice were sublethally irradiated to 4.5 Gy and injected with an MLL-ENL and NRAS syngeneic leukemia. Once engraftment was established by bioluminescence imaging, mice were treated with 300 mg/kg FdUMP[10] via jugular vein injection on days 1 and 4. (B) Kaplan-Meier curves for animals treated with FdUMP[10] as above versus no treatment. P value was obtained by log rank test. (C) Kaplan-Meier curves for animals treated with FdUMP[10] at 300 mg/kg every other day for 4 doses by tail vein injection. P value was obtained by log rank test.
Figure 12:
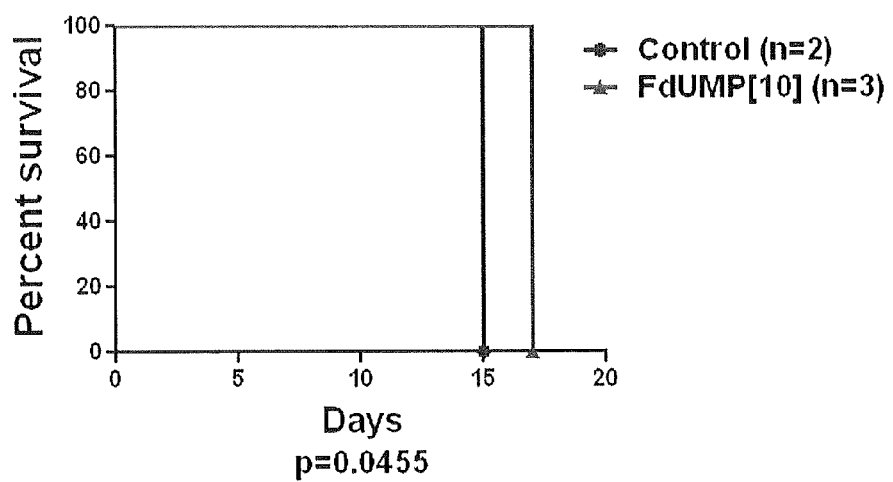
Figure 12:
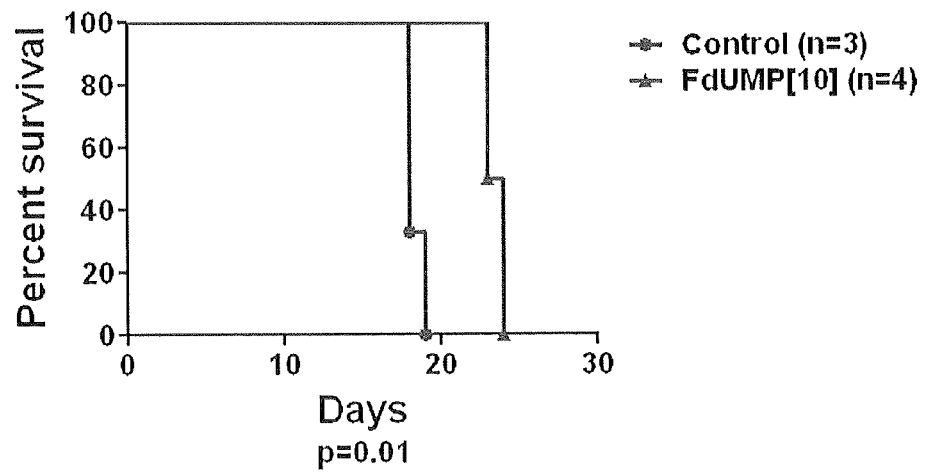

Recent studies have shown that the bone marrow microenvironment can have a profound effect on chemotherapy response in AML[24]. Additionally, the immune system can affect the degree of response to a given therapy in vivo[25]. To assess the activity of FdUMP[10] in a setting that would incorporate these important interactions, we injected sublethally irradiated C57/Bl6 mice with the MR2 cell line. This cell line express MLL-ENL and the mutated oncogene, $NRas^{G12D}$ in conjunction with a luciferase reporter. Once leukemic engraftment was confirmed by bioluminescence imaging, mice were treated. When mice were treated with FdUMP[10] at 300 mg/kg on days 1 and 4, there was reduction in disease burden (FIG. 12A) and a statistically significant survival benefit when compared to untreated controls (FIG. 12B). FdUMP[10]-treated mice showed no signs of toxicity. To determine if we could improve survival, we treated MR2-injected mice with FdUMP[10] at 300 mg/kg every other day for four doses. This increased dosing regimen was well tolerated and resulted in a significant survival benefit (FIG. 12C). In order to establish efficacy of FdUMP[10] in a second MLL-ENL leukemia and to compare it to equivalently dosed 5-FU or Ara-C and doxorubicin (Ara/Dox), mice were injected with the MFL2 cell line. This cell line expresses the FLT3 receptor with an internal tandem duplication (FLT3 ITD) in place of $NRas^{G12D}$. Treatment consisted of either FdUMP[10] (300 mg/kg), 5-FU (121 mg/kg) or Ara-C (125 mg/kg) plus doxorubicin (3.75 mg/kg) on days 1, 3, 5, and 7 (FIG. 1A). The 5-FU dose was calculated to deliver the same FP content as FdUMP[10] dosed at 300 mg/kg. The Ara/Dox doses were designed to deliver the same amount of both drugs as in the previously published regimen shown to be tolerable and efficacious[26]. FdUMP[10] treatment resulted in reduced disease burden as determined by bioluminescent imaging (FIG. 1B) and improved survival when compared to controls (p=0.0002, FIG. 1C). There was no difference in survival between FdUMP[10]-treated and Ara/Dox treated animals (p=0.604, FIG. 1C), suggesting comparable efficacy. In contrast treatment with 5-FU resulted in early deaths and no survival benefit over controls (p=0.24, FIG. 1C). These data demonstrate that FdUMP[10] as a single agent is as active as combination therapy with Ara/Dox. The increased toxicity and early deaths seen with 5-FU but not FdUMP[10] treatment demonstrate that in vivo FdUMP[10] is not simply catabolized to the 5-FU moiety but rather behaves as a distinct chemical entity.

FdUMP[10] Causes Less Toxicity than Either 5-FU or Cytarabine Plus Doxorubicin and Spares Normal HSCs.

Figure 6:
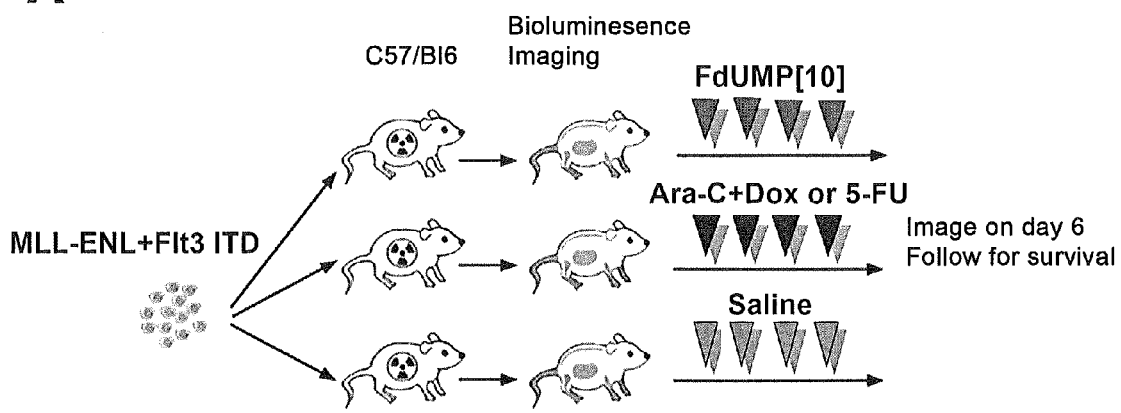
FIG. 6. FdUMP[10] confers a survival benefit equivalent to the combination of Ara-C and doxorubicin. A) Schema of treatment trial. C57/Bl6 mice were sublethally irradiated to 4.5 Gy and injected with an MLL-ENL and Fms-like tyrosine kinase 3 internal tandem duplication (FLT3-ITD) syngeneic leukemia. Once engraftment was established by bioluminescence imaging, mice were treated with either saline (S), FdUMP[10] at 300 mg/kg (Fd), 5-FU at 121 mg/kg or cytarabine at 125 mg/kg plus doxorubicin at 3.75 mg/kg (AD) on days 1, 3, 5, and 7. (B) Bioluminescent image of mice on day 6 following treatment. (C) Kaplan-Meier curves for animals treated with Fd, 5-FU or AD as above.
Figure 6:
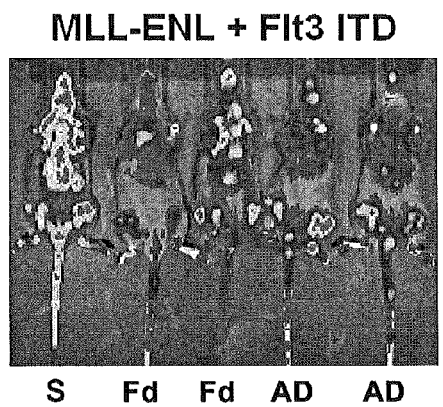
Figure 6:
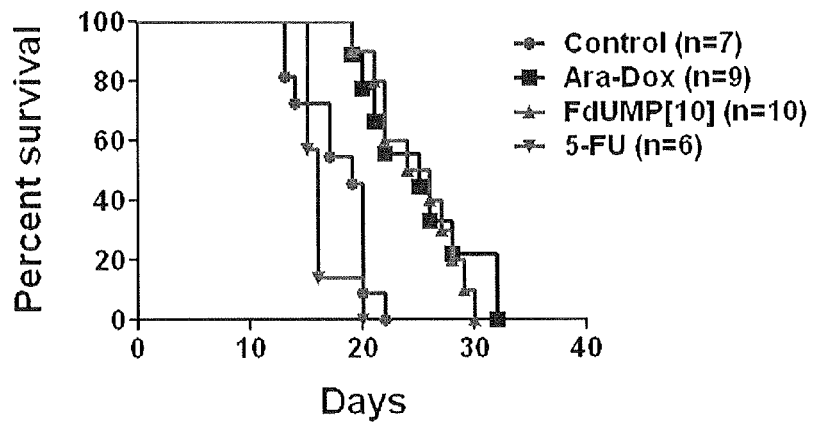
Figure 7:
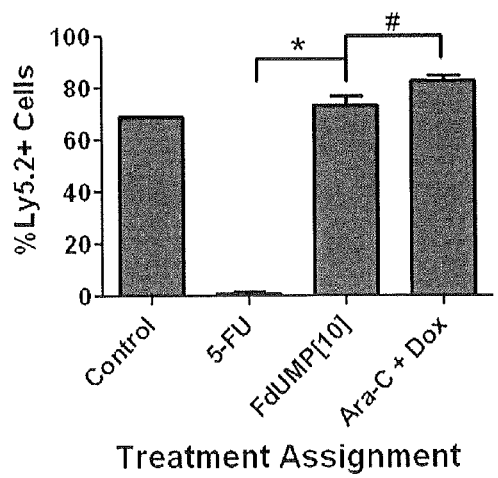
FIG. 7. FdUMP[10] induces less toxicity than either 5-FU or cytarabine plus doxorubicin. (A) Hematoxylin and eosin staining of organs from mice treated with either FdUMP[10], 5-FU, or cytarabine plus doxorubicin (Ara-Dox). Mice were treated in the same manner as the in FIG. 6; sacrificed 72 hours after the last dose; and organs were harvested, fixed, paraffin-embedded, sectioned, and stained. Slides were imaged using a Nikon Eclipse 50i light microscope, magnification as indicated. Photographs of tissues were taken using the NIS Elements D3.10 camera and software system. (B) Bone marrow transplant. Donor mice were treated with either 5-FU, FdUMP[10] or Ara-C+doxorubicin as above and 72 hours after last does animals were sacrificed and b/l femur cells harvested. Ly5.1+C57/Bl6 recipient mice were irradiated to 8 gray and injected with donor cells. After three weeks recipients were harvested and degree of femur engraftment by donor cells was determined by staining with Ly5.2 antibody and analyzed by flow cytometry.

Previous studies have shown that the gastrointestinal (GI) toxicity caused by 5-FU is at least in part mediated by RNA-directed effects[27]. As FdUMP[10] is primarily metabolized to the DNA-directed metabolite, FdUMP, it should exhibit reduced GI toxicity compared to 5-FU. To compare the toxicity of FdUMP[10] to 5-FU and Ara/Dox, we treated C57/Bl6 mice with these agents as in the efficacy studies with animals dosed on days 1, 3, 5 and 7. Three days after the last treatment, animals were sacrificed, bilateral femur marrow cells collected and organs harvested, sectioned, and stained. Tissues most affected were the small intestine, colon, and the bone marrow. In the GI-tract, the 5-FU-treated animals had severe villous blunting and fusion with crypt necrosis in both large and small intestine (FIG. 6A). In contrast, FdUMP[10]-treated animals had only mild crypt epithelial apoptosis with mitoses. The 5-FU and Ara/Dox groups had severe pancytopenia in the marrow compared to FdUMP[10]-treated animals that showed only minimal to mild apoptosis (FIG. 6A).

To assess the impact of FdUMP[10] on normal murine HSCs, harvested femur cells were counted and $1 \times 10^6$ cells were injected into Ly5.1+C57/Bl6 mice irradiated to 8 gray. In the 5-FU treated animals $1 \times 10^6$ cells could not be harvested, so 90% of all cells collected were injected. Three weeks later the recipients were sacrificed, bone marrow harvested and stained for Ly5.2 to determine the extent of engraftment. Cells from mice treated with FdUMP[10] engrafted to the same extent as the control animal and the level of engraftment was not significantly different from animals treated with Ara/Dox (p=0.083, FIG. 6B). In contrast, the cells from the 5-FU treated animals showed only minimal engraftment. These data suggest that despite the enhanced activity of FdUMP[10] against AML, there is in fact less toxicity when compared to 5-FU or Ara/Dox. The fact that bone marrow cells from FdUMP[10] treated animals efficiently engrafted in recipients suggests a large therapeutic window and provides further evidence that its mechanism of action is distinct from 5-FU.

Discussion

AML is an aggressive malignancy with poor outcomes. Despite decades of research, therapy has remained largely unchanged. AML is primarily a disease of the elderly, with a median age of onset of 72 years[5]; and remissions come at the cost of considerable toxicity. In a recent report of older patients treated with standard therapy, 32% of patients either died or could not receive additional therapy because of severe morbidity[4]. In elderly patients who do not die from treatment-related toxicity or resistant disease, remissions are short-lived, with median survival times of only ~12 months[5]. Novel agents are critically needed. To this end we tested the activity of the novel polymeric fluoropyrimidine, FdUMP[10]. This compound is a deoxyoligonucleotide made up entirely of the TS-inhibitory metabolite of 5-FU, FdUMP. As a deoxyoligonucleotide it would be predicted to have distinct uptake and metabolic breakdown products with an increase in the production of the DNA-directed metabolite, FdUMP, as compared to 5-FU. Consistent with this, FdUMP[10] demonstrated a 338-fold increase in potency against the NCI 60 cell line screen and decreased toxicity compared to 5-FU[8,28]. Additionally, FdUMP[10] has demonstrated efficacy against malignancies not typically treated with 5-FU[9,29]. When we tested FdUMP[10] against several pre-clinical models of AML we made several important observations.

First, FdUMP[10] was highly cytotoxic against multiple human leukemia cell lines with $IC_{50}$ values lower than those for doxorubicin or Ara-C. Importantly it demonstrated an ~1,000 fold increased potency compared to 5-FU despite having only 10 times the FP content suggesting a distinct mechanism of action. Second, the cytotoxicity of FdUMP[10] was not dramatically affected by several factors shown to contribute to resistance to standard therapies or confer an adverse prognosis. FdUMP[10] was extremely potent in MLL-ENL expressing murine AML cells, including those expressing the Flt3 ITD. The presence of an shRNA that targets p53 did not affect response to FdUMP[10] despite the fact that it conferred resistance to both doxorubicin and Ara-C. Likewise when murine AML cells expressed high levels of MN1 or BCR-ABL, conferring resistance to both cytarabine and doxorubicin, only minimal changes were noted in FdUMP[10] response. Third, FdUMP[10] inhibited leukemia stem cells derived from both human cell lines and three primary patient samples while sparing normal human HSC colony formation. Fourth, FdUMP[10] demonstrated profound TS inhibition, trapping of Top1CC, DNA damage and induction of apoptosis. Importantly 5-FU did not display these activities despite being used at doses that would deliver the same or more FP content demonstrating that FdUMP[10] exhibits a distinct mechanism of action with dual TS- and Top1-directed activity. All human leukemia cell lines and virtually all patient samples expressed both targets suggesting FdUMP[10] is likely to have broad activity in AML. Finally, FdUMP[10] was found to have in vivo activity against two MLL-ENL expressing, syngeneic mouse leukemias that was equivalent to the combination of Ara-C and doxorubicin. This activity did not come at the cost of increased toxicity as animals treated with FdUMP[10] demonstrated the least GI and bone marrow toxicity when compared to Ara-C and doxorubicin or 5-FU treated animals. Indeed marrow cells taken from FdUMP[10] treated animals engrafted well into irradiated recipients, in contrast to 5-FU treated animals where little to no engraftment was detected.

These data demonstrate that FdUMP[10] is not simply a delivery vehicle for 5-FU but has a distinct mechanism of action. This is in agreement with previous studies[8,28,30] including a recent genome-wide profiling study for determinants of sensitivity to FdUMP[10] that revealed expression of genes involved in endocytosis as important for activity, arguing the molecule is taken up whole[29]. Consistent with FdUMP[10] having a unique mechanism of action we demonstrated it efficiently traps Top1CC, an activity not ascribed to 5-FU. The notion that FdUMP[10] acts at least in part as a Top1 poison is supported by the fact that a COMPARE analysis done with the NCI 60 cell line panel revealed the top four similar drugs were all camptothecin derivatives[9]. This is consistent with the fact that camptothecins have activity in AML, as shown in several clinical trials[31-33].

The data support the hypothesis that FdUMP[10] is taken up by AML cells, converted to the TS inhibitory metabolite FdUMP, and causes simultaneous DNA damage and nucleotide imbalances that make repair impossible. This dual activity suggests that cells with impaired DNA damage responses that can confer resistance to DNA damaging agents will not be resistant to FdUMP[10] as the damage must be repaired to resolve the trapped Top1CCs before cells can complete S-phase. The fact that p53 loss did not affect response to FdUMP[10] is consistent with this hypothesis.

The improved toxicity profile of FdUMP[10] may be explained by the fact that Top1 trapping activity requires incorporation of FdUMP or dUMP into DNA by actively replicating cells. This is in contrast to 5-FU, which causes ribosomal stress and inhibits RNA processing, and camptothecins, which cause DNA DSBs as a result of trapping Top1 cleavage complexes in transcriptionally active, non-replicating cells. Similarly, the anthracyclines can induce DNA damage in cells regardless of cell-cycle phase, leading to increased toxicity. The reduced systemic toxicity for FdUMP[10] relative to 5-FU observed in our studies likely results from reduced RNA-directed effects.

In the last three decades the standard therapy for remission induction in AML has not changed[2]. The unique mechanism of action for FdUMP[10] with dual targeting of TS and Top1 results in strong efficacy even when cells expressed several markers of poor prognosis. This taken together with the reduced systemic toxicity make FdUMP[10] an ideal candidate for translation to the clinic. Thus, FdUMP[10] is likely to have broad clinical activity in AML and to provide a less toxic alternative to the current standard of care applicable to most, if not all AML patients.

REFERENCES

1. Licht J D, Sternberg D W. The molecular pathology of acute myeloid leukemia. *Hematology Am Soc Hematol Educ Program.* 2005:137-142.

2. Dohner H, Estey E H, Amadori S, et al. Diagnosis and management of acute myeloid leukemia in adults: recommendations from an international expert panel, on behalf of the European LeukemiaNet. *Blood.* 2010; 115(3):453-474.
3. Appelbaum F R, Gundacker H, Head D R, et al. Age and acute myeloid leukemia. *Blood.* 2006; 107(9):3481-3485.
4. Rollig C, Thiede C, Gramatzki M, et al. A novel prognostic model in elderly patients with acute myeloid leukemia: results of 909 patients entered into the prospective AML96 trial. *Blood.* 2010; 116(6):971-978.
5. Juliusson G, Antunovic P, Derolf A, et al. Age and acute myeloid leukemia: real world data on decision to treat and outcomes from the Swedish Acute Leukemia Registry. *Blood.* 2009; 113(18):4179-4187.
6. Kantarjian H, Ravandi F, O'Brien S, et al. Intensive chemotherapy does not benefit most older patients (age 70 years or older) with acute myeloid leukemia. *Blood.* 2010.
7. Longley D B, Harkin D P, Johnston P G. 5-fluorouracil: mechanisms of action and clinical strategies. *Nat Rev Cancer.* 2003; 3(5):330-338.
8. Gmeiner W H, Skradis A, Pon R T, Liu J. Cytotoxicity and in-vivo tolerance of FdUMP[10]: a novel pro-drug of the TS inhibitory nucleotide FdUMP. *Nucleosides Nucleotides.* 1999; 18(6-7):1729-1730.
9. Liao Z Y, Sordet O, Zhang H L, et al. A novel polypyrimidine antitumor agent FdUMP[10] induces thymineless death with topoisomerase I-DNA complexes. *Cancer Res.* 2005; 65(11):4844-4851.
10. Pardee T S, Zuber J, Lowe S W. The Flt3 Internal Tandem Duplication Alters Chemotherapy Response In Vitro and In Vivo in a p53-Dependent Manner. *Exp Hematol.* 2011.
11. Zuber J, Radtke I, Pardee T S, et al. Mouse models of human AML accurately predict chemotherapy response. *Genes Dev.* 2009; 23(7):877-889.
12. Lee B D, Sevcikova S, Kogan S C. Dual treatment with FLT3 inhibitor SU11657 and doxorubicin increases survival of leukemic mice. *Leuk Res.* 2007; 31(8):1131-1134.
13. Schlenk R F, Dohner K, Krauter J, et al. Mutations and treatment outcome in cytogenetically normal acute myeloid leukemia. *N Engl J Med.* 2008; 358(18):1909-1918.
14. Yin B, Kogan S C, Dickins R A, Lowe S W, Largaespada D A. Trp53 loss during in vitro selection contributes to acquired Ara-C resistance in acute myeloid leukemia. *Exp Hematol.* 2006; 34(5):631-641.
15. Ravizza R, Gariboldi M B, Passarelli L, Monti E. Role of the p53/p21 system in the response of human colon carcinoma cells to Doxorubicin. *BMC Cancer.* 2004; 4:92.
16. Seifert H, Mohr B, Thiede C, et al. The prognostic impact of 17p (p53) deletion in 2272 adults with acute myeloid leukemia. *Leukemia.* 2009.
17. Nahi H, Lehmann S, Bengtzen S, et al. Chromosomal aberrations in 17p predict in vitro drug resistance and short overall survival in acute myeloid leukemia. *Leuk Lymphoma.* 2008; 49(3):508-516.
18. Cotter TG. BCR-ABL: an anti-apoptosis gene in chronic myelogenous leukemia. *Leuk Lymphoma.* 1995; 18(3-4):231-236.
19. Soupir C P, Vergilio J A, Dal Cin P, et al. Philadelphia chromosome-positive acute myeloid leukemia: a rare aggressive leukemia with clinicopathologic features distinct from chronic myeloid leukemia in myeloid blast crisis. *Am J Clin Pathol.* 2007; 127(4):642-650.
20. Liu T, Jankovic D, Brault L, et al. Functional characterization of high levels of meningioma 1 as collaborating oncogene in acute leukemia. *Leukemia.* 2010; 24(3):601-612.
21. Heuser M, Beutel G, Krauter J, et al. High meningioma 1 (MN1) expression as a predictor for poor outcome in acute myeloid leukemia with normal cytogenetics. *Blood.* 2006; 108(12):3898-3905.
22. Langer C, Marcucci G, Holland K B, et al. Prognostic importance of MN1 transcript levels, and biologic insights from MN1-associated gene and microRNA expression signatures in cytogenetically normal acute myeloid leukemia: a cancer and leukemia group B study. *J Clin Oncol.* 2009; 27(19):3198-3204.
23. Chan W I, Huntly B J. Leukemia stem cells in acute myeloid leukemia. *Semin Oncol.* 2008; 35(4):326-335.
24. Gmeiner W H, Trump E, Wei C. Enhanced DNA-directed effects of FdUMP[10] compared to 5FU. *Nucleosides Nucleotides Nucleic Acids.* 2004; 23(1-2):401-410.
25. Nervi B, Ramirez P, Rettig M P, et al. Chemosensitization of acute myeloid leukemia (AML) following mobilization by the CXCR4 antagonist AMD3100. *Blood.* 2009; 113(24):6206-6214.
26. Majeti R, Chao M P, Alizadeh A A, et al. CD47 is an adverse prognostic factor and therapeutic antibody target on human acute myeloid leukemia stem cells. *Cell.* 2009; 138(2):286-299.
27. Pritchard D M, Watson A J, Potten C S, Jackman A L, Hickman J A. Inhibition by uridine but not thymidine of p53-dependent intestinal apoptosis initiated by 5-fluorouracil: evidence for the involvement of RNA perturbation. *Proc Natl Acad Sci USA.* 1997; 94(5):1795-1799.
28. Liu J, Skradis A, Kolar C, et al. Increased cytotoxicity and decreased in vivo toxicity of FdUMP[10] relative to 5-FU. *Nucleosides Nucleotides.* 1999; 18(8): 1789-1802.
29. Gmeiner W H, Reinhold W C, Pommier Y. Genome-wide mRNA and microRNA profiling of the NCI 60 cell-line screen and comparison of FdUMP[10] with fluorouracil, floxuridine, and topoisomerase 1 poisons. *Mol Cancer Ther.* 2010; 9(12):3105-3114.
30. Liu C, Willingham M, Liu J, Gmeiner W H. Efficacy and safety of FdUMP[10] in treatment of HT-29 human colon cancer xenografts. *Int J Oncol.* 2002; 21(2):303-308.
31. Minderman H, O'Loughlin K L, Smith P F, et al. Sequential administration of irinotecan and cytarabine in the treatment of relapsed and refractory acute myeloid leukemia. *Cancer Chemother Pharmacol.* 2006; 57(1):73-83.
32. Weihrauch M R, Staib P, Seiberlich B, Hoffmann M, Diehl V, Tesch H. Phase I/II clinical study of topotecan and cytarabine in patients with myelodysplastic syndrome, chronic myelomonocytic leukemia and acute myeloid leukemia. *Leuk Lymphoma.* 2004; 45(4):699-704.
33. Bolanos-Meade J, Guo C, Gojo I, Karp J E. A phase II study of timed sequential therapy of acute myelogenous leukemia (AML) for patients over the age of 60: two cycle timed sequential therapy with topotecan, ara-C and mitoxantrone in adults with poor-risk AML. *Leuk Res.* 2004; 28(6):571-577.
34. Timeus F, Crescenzio N, Ricotti E, et al. The effects of saquinavir on imatinib-resistant chronic myelogenous leukemia cell lines. *Haematologica.* 2006; 91(5):711-712.
35. Bailly J D, Muller C, Jaffrezou J P, et al. Lack of correlation between expression and function of P-glycoprotein in acute myeloid leukemia cell lines. *Leukemia.* 1995; 9(5): 799-807.
36. Ju J F, Banerjee D, Lenz H J, et al. Restoration of wild-type p53 activity in p53-null HL-60 cells confers multidrug sensitivity. *Clin Cancer Res.* 1998; 4(5):1315-1322.

The foregoing is illustrative of the present invention, and is not to be construed as limiting thereof. The invention is defined by the following claims, with equivalents of the claims to be included therein.

What is claimed is:

1. A method of treating acute myelogenous leukemia (AML) in a subject in need thereof, comprising administering said subject an active compound in an amount effective to treat said leukemia, wherein said active compound is a 10-mer oligonucleotide of 5-fluoro-2'-deoxyuridine-5'-monophosphate (FdUMP[10]) or a pharmaceutically acceptable salt thereof.

2. The method of claim 1, wherein said subject is a human subject.

3. The method of claim 1, wherein said AML is:
   selected from the group consisting of therapy-related AML, AML with multilineage dysplasia, and AML with characteristic genetic abnormalities (WHO classification); or
   selected from a group consisting of minimally differentiated acute myeloblastic leukemia, acute myeloblastic leukemia without maturation, acute myeloblastic leukemia with granulocytic maturation, acute promyelocytic leukemia, acute myelomonocytic leukemia, myelomonocytic together with bone marrow eosinophilia, acute monoblastic leukemia, acute monocytic leukemia, acute erythroid leukemia, acute megakaryoblastic leukemia, and acute basophilic leukemia (French-American British (FAB) classification).

4. The method of claim 1, wherein said active compound is administered to said subject intravenously in an amount of from 100 to 1000 mg/m$^2$.

5. The method of claim 2, wherein said subject is at least 60, 65 or 70 years old.

6. The method of claim 1, wherein the active compound administered is a single active compound consisting of FdUMP[10] or a pharmaceutically acceptable salt thereof in an amount effective to treat said leukemia.

7. The method of claim 2, further comprising wherein said subject is classified in a good prognostic risk category.

8. The method of claim 2, further comprising wherein said subject is classified in an intermediate prognostic risk category.

9. The method of claim 2, further comprising wherein said subject is classified in a poor prognostic risk category.

10. The method of claim 2, further comprising wherein said subject has or expresses: a mixed lineage leukemia (MLL) fusion protein, the breakpoint cluster region-Abelson murine leukemia viral oncogene homolog 1 (BCR-ABL) fusion protein, Fms-like tyrosine kinase 3 (FLT3) internal tandem duplications, a deleted or mutated p53, high or elevated levels of meningioma 1, and/or high or elevated levels of lactate dehydrogenase.

11. The method of claim 2, further comprising wherein said AML is relapsed AML.

12. A method of treating acute myelogenous leukemia (AML) in a subject in need thereof, comprising:
   determining whether said subject is classified in a good, intermediate, or poor prognostic risk category for said AML, and then, if said subject is in an intermediate or poor prognostic risk category
   administering said subject an active compound in an amount effective to treat said leukemia, wherein said active compound is a 10-mer oligonucleotide of 5-fluoro-2'-deoxyuridine-5'-monophosphate (FdUMP[10]) or a pharmaceutically acceptable salt thereof.

13. The method of claim 12, wherein said subject is a human subject.

14. The method of claim 12, wherein said AML is:
   selected from the group consisting of therapy-related AML, AML with multilineage dysplasia, and AML with characteristic genetic abnormalities (WHO classification); or
   selected from a group consisting of minimally differentiated acute myeloblastic leukemia, acute myeloblastic leukemia without maturation, acute myeloblastic leukemia with granulocytic maturation, acute promyelocytic leukemia, acute myelomonocytic leukemia, myelomonocytic together with bone marrow eosinophilia, acute monoblastic leukemia, acute monocytic leukemia, acute erythroid leukemia, acute megakaryoblastic leukemia, and acute basophilic leukemia (French-American British (FAB) classification).

15. The method of claim 12, wherein said active compound is administered to said subject intravenously in an amount of from 100 to 1000 mg/m$^2$.

16. The method of claim 13, wherein said subject is at least 60, 65 or 70 years old.

17. The method of claim 12, wherein the active compound administered is a single active compound consisting of FdUMP[10] or a pharmaceutically acceptable salt thereof in an amount effective to treat said leukemia.

18. The method of claim 13, wherein said subject is classified in a poor prognostic risk category.

19. The method of claim 13, further comprising wherein said subject has or expresses: a mixed lineage leukemia (MLL) fusion protein, the breakpoint cluster region-Abelson murine leukemia viral oncogene homolog 1 (BCR-ABL) fusion protein, Fms-like tyrosine kinase 3 (FLT3) internal tandem duplications, a deleted or mutated p53, high or elevated levels of meningioma 1, and/or high or elevated levels of lactate dehydrogenase.

20. The method of claim 13, further comprising wherein said AML is relapsed AML.

* * * * *

UNITED STATES PATENT AND TRADEMARK OFFICE
CERTIFICATE OF CORRECTION

PATENT NO. : 9,012,422 B2
APPLICATION NO. : 13/565108
DATED : April 21, 2015
INVENTOR(S) : Gmeiner et al.

It is certified that error appears in the above-identified patent and that said Letters Patent is hereby corrected as shown below:

In the Specification

Column 5, Lines 1-20: Please replace the structure in its entirety with the structure below:

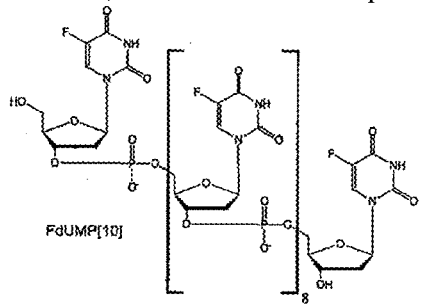

Column 13: Please replace the footnote table below:
MFL2= MLL-ENL + Flt3-ITD
MR2= MLL-ENL + NRas$^{G12D}$
M1= MLL-ENL alone
95% confidence intervals are shown in the parenthesis.

With:
MFL2=MLL-ENL+FLT3-ITD
MR2=MLL-ENL+NRAS$^{G12D}$
M1=MLL-ENL alone
95% confidence intervals are shown in the parenthesis.

Signed and Sealed this
Third Day of April, 2018

Andrei Iancu
*Director of the United States Patent and Trademark Office*

UNITED STATES PATENT AND TRADEMARK OFFICE
CERTIFICATE OF CORRECTION

PATENT NO. : 9,012,422 B2
APPLICATION NO. : 13/565108
DATED : April 21, 2015
INVENTOR(S) : Gmeiner et al.

Page 1 of 1

It is certified that error appears in the above-identified patent and that said Letters Patent is hereby corrected as shown below:

In the Specification

Column 1, Line 12 STATEMENT REGARDING GOVERNMENT SUPPORT:
Delete the paragraph in its entirety and replace with:
-- This invention was made with government support under P30CA012197 and CA102532 awarded by the National Institutes of Health. The government has certain rights in the invention. --

Signed and Sealed this
Twenty-ninth Day of January, 2019

Andrei Iancu
*Director of the United States Patent and Trademark Office*

UNITED STATES PATENT AND TRADEMARK OFFICE
CERTIFICATE OF CORRECTION

PATENT NO. : 9,012,422 B2
APPLICATION NO. : 13/565108
DATED : April 21, 2015
INVENTOR(S) : Gmeiner et al.

It is certified that error appears in the above-identified patent and that said Letters Patent is hereby corrected as shown below:

In the Specification

Column 1, Lines 15-18: Please delete the paragraph below the STATEMENT REGARDING GOVERNMENT SUPPORT and insert the following:
--This invention was made with government support under CA102532, and P30 CA012197 awarded by the National Institutes of Health. The government has certain rights in the invention.--

This certificate supersedes the Certificate of Correction issued January 29, 2019.

Signed and Sealed this
Ninth Day of May, 2023

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 10
<212> TYPE: DNA
<213> ORGANISM: Artificial
<220> FEATURE:
<223> OTHER INFORMATION: FdUMP[10] sequence
<220> FEATURE:
<221> NAME/KEY: misc_feature
<222> LOCATION: (1)..(10)
<223> OTHER INFORMATION: n is 5-fluorodeoxyuracil
<220> FEATURE:
<221> NAME/KEY: misc_feature
<222> LOCATION: (1)..(10)
<223> OTHER INFORMATION: n is 5-fluorodeoxyuridine

<400> SEQUENCE: 1 nnnnnnnnnn                                                    10
```